United States Patent
Kato et al.

(10) Patent No.: US 11,901,043 B2
(45) Date of Patent: Feb. 13, 2024

(54) SEQUENCE ANALYSIS METHOD, SEQUENCE ANALYSIS APPARATUS, REFERENCE SEQUENCE GENERATION METHOD, REFERENCE SEQUENCE GENERATION APPARATUS, PROGRAM, AND STORAGE MEDIUM

(71) Applicants: National Cancer Center, Tokyo (JP); MITSUI KNOWLEDGE INDUSTRY CO., LTD., Tokyo (JP); SYSMEX CORPORATION, Kobe (JP)

(72) Inventors: Mamoru Kato, Tokyo (JP); Hideya Kuwabara, Tokyo (JP); Tomohiro Sakuma, Tokyo (JP); Fumio Inoue, Kobe (JP); Kenichiro Suzuki, Kobe (JP)

(73) Assignees: National Cancer Center, Tokyo (JP); Mitsui Knowledge Industry Co., Ltd., Tokyo (JP); Sysmex Corporation, Kobe (JP)

( * ) Notice: Subject to any disclaimer, the term of this patent is extended or adjusted under 35 U.S.C. 154(b) by 902 days.

(21) Appl. No.: 16/185,987

(22) Filed: Nov. 9, 2018

(65) Prior Publication Data
US 2019/0156914 A1    May 23, 2019

(30) Foreign Application Priority Data
Nov. 9, 2017    (JP) .................................. 2017-216502

(51) Int. Cl.
G16B 20/20    (2019.01)
C12Q 1/6827    (2018.01)
(Continued)

(52) U.S. Cl.
CPC ........... *G16B 20/20* (2019.02); *C12Q 1/6827* (2013.01); *C12Q 1/6869* (2013.01); *G16B 20/10* (2019.02);
(Continued)

(58) Field of Classification Search
CPC ........ G16B 20/20; G16B 30/10; G16B 50/30; G16B 50/20; C12Q 1/6869; C12Q 1/6827
(Continued)

(56) References Cited

U.S. PATENT DOCUMENTS

2012/0208706 A1    8/2012    Downing et al.
2014/0066317 A1    3/2014    Talasaz
(Continued)

FOREIGN PATENT DOCUMENTS

CN    102766688 A    11/2012
CN    103797486 A    5/2014
(Continued)

OTHER PUBLICATIONS

DbSNP: a database of single nucleotide polymorphism, Elizabeth M Smigielski et al. Nucleic Acids Research, vol. 28, pp. 352-355. (Year: 2000).*
(Continued)

*Primary Examiner* — Larry D Riggs, II
*Assistant Examiner* — Guozhen Liu
(74) *Attorney, Agent, or Firm* — Crowell & Moring LLP

(57) ABSTRACT

Disclosed is a sequence analysis method for analyzing nucleic acid sequence, the sequence analysis method including: obtaining a plurality of read sequences read from the nucleic acid sequence; and determining each nucleic acid sequence by aligning each read sequence with reference to a single reference sequence, wherein the reference sequence
(Continued)

includes at least a first rearrangement sequence and a second rearrangement sequence that is different from the first rearrangement sequence.

21 Claims, 27 Drawing Sheets

Specification includes a Sequence Listing.

(51) Int. Cl.
| | |
|---|---|
| C12Q 1/6869 | (2018.01) |
| G16B 30/00 | (2019.01) |
| G16B 30/10 | (2019.01) |
| G16B 50/20 | (2019.01) |
| G16B 50/30 | (2019.01) |
| G16B 20/10 | (2019.01) |
| G16B 30/20 | (2019.01) |
| G16B 20/00 | (2019.01) |

(52) U.S. Cl.
CPC .............. *G16B 30/00* (2019.02); *G16B 30/10* (2019.02); *G16B 30/20* (2019.02); *G16B 50/20* (2019.02); *G16B 50/30* (2019.02); *G16B 20/00* (2019.02)

(58) Field of Classification Search
USPC .......................................................... 702/19
See application file for complete search history.

(56) References Cited

U.S. PATENT DOCUMENTS

| | | |
|---|---|---|
| 2014/0149049 A1 | 5/2014 | Chen et al. |
| 2014/0249764 A1 | 9/2014 | Kumar et al. |
| 2014/0336941 A1 | 11/2014 | Park |
| 2015/0056613 A1 | 2/2015 | Kural |
| 2015/0057946 A1 | 2/2015 | Kural |
| 2015/0199472 A1 | 7/2015 | Kural |
| 2015/0211047 A1 | 7/2015 | Borns |
| 2015/0299812 A1 | 10/2015 | Talasaz |
| 2015/0347678 A1 | 12/2015 | Kural |
| 2015/0368708 A1 | 12/2015 | Talasaz |
| 2016/0017405 A1 | 1/2016 | Borns |
| 2016/0040229 A1 | 2/2016 | Talasaz et al. |
| 2016/0046986 A1 | 2/2016 | Eltoukhy et al. |
| 2016/0092630 A1 | 3/2016 | Chen et al. |
| 2016/0251704 A1 | 9/2016 | Talasaz et al. |
| 2016/0306921 A1 | 10/2016 | Kural |
| 2016/0333417 A1 | 11/2016 | Talasaz |
| 2016/0340722 A1 | 11/2016 | Platt |
| 2017/0218459 A1 | 8/2017 | Talasaz et al. |
| 2017/0218460 A1 | 8/2017 | Talasaz |
| 2018/0023125 A1 | 1/2018 | Talasaz et al. |
| 2018/0171415 A1 | 6/2018 | Talasaz et al. |
| 2018/0223374 A1 | 8/2018 | Talasaz et al. |
| 2018/0230530 A1 | 8/2018 | Eltoukhy et al. |
| 2018/0327862 A1 | 11/2018 | Talasaz et al. |
| 2018/0336314 A1 | 11/2018 | Kural |
| 2018/0357367 A1 | 12/2018 | Kural |
| 2019/0078164 A1 | 3/2019 | Talasaz |
| 2019/0177802 A1 | 6/2019 | Talasaz |
| 2019/0177803 A1 | 6/2019 | Talasaz |
| 2019/0185940 A1 | 6/2019 | Talasaz |
| 2019/0185941 A1 | 6/2019 | Talasaz |
| 2019/0272891 A1 | 9/2019 | Kural |
| 2019/0316185 A1 | 10/2019 | Talasaz et al. |
| 2020/0032323 A1 | 1/2020 | Talasaz et al. |
| 2020/0087735 A1 | 3/2020 | Talasaz |
| 2020/0087736 A1 | 3/2020 | Talasaz |
| 2020/0115739 A1 | 4/2020 | Talasaz et al. |
| 2020/0115746 A1 | 4/2020 | Talasaz et al. |
| 2020/0123602 A1 | 4/2020 | Eltoukhy et al. |
| 2020/0131568 A1 | 4/2020 | Talasaz et al. |
| 2020/0168295 A1 | 5/2020 | Kural |
| 2020/0224254 A1 | 7/2020 | Talasaz et al. |
| 2020/0248270 A1 | 8/2020 | Talasaz |
| 2020/0263239 A1 | 8/2020 | Talasaz et al. |
| 2020/0291487 A1 | 9/2020 | Talasaz |
| 2020/0299756 A1 | 9/2020 | Talasaz et al. |
| 2020/0299785 A1 | 9/2020 | Talasaz |
| 2020/0325529 A1 | 10/2020 | Talasaz et al. |
| 2020/0362405 A1 | 11/2020 | Talasaz et al. |
| 2021/0032707 A1 | 2/2021 | Talasaz |
| 2021/0040545 A1 | 2/2021 | Talasaz et al. |
| 2021/0087616 A1 | 3/2021 | Talasaz et al. |
| 2021/0102243 A1 | 4/2021 | Talasaz et al. |
| 2021/0130912 A1 | 5/2021 | Talasaz |
| 2021/0139998 A1 | 5/2021 | Talasaz |
| 2021/0164037 A1 | 6/2021 | Talasaz et al. |
| 2021/0340632 A1 | 11/2021 | Talasaz |
| 2021/0355549 A1 | 11/2021 | Talasaz |
| 2021/0371912 A1 | 12/2021 | Talasaz et al. |
| 2021/0395814 A1 | 12/2021 | Talasaz et al. |
| 2022/0042104 A1 | 2/2022 | Talasaz |
| 2022/0049299 A1 | 2/2022 | Talasaz et al. |
| 2022/0049300 A1 | 2/2022 | Talasaz et al. |
| 2022/0119880 A1 | 4/2022 | Talasaz et al. |
| 2022/0145385 A1 | 5/2022 | Talasaz et al. |
| 2022/0205051 A1 | 6/2022 | Talasaz |
| 2022/0325340 A1 | 10/2022 | Talasaz et al. |
| 2022/0380842 A1 | 12/2022 | Talasaz et al. |
| 2022/0389489 A1 | 12/2022 | Talasaz et al. |

FOREIGN PATENT DOCUMENTS

| | | |
|---|---|---|
| CN | 104781421 A | 7/2015 |
| CN | 105637098 A | 6/2016 |
| CN | 105793689 A | 7/2016 |
| CN | 105793859 A | 7/2016 |
| EP | 3097206 A1 | 11/2016 |
| JP | 2014-507133 A | 3/2014 |
| JP | 2015-180193 | 10/2015 |
| JP | 2015-536661 A | 12/2015 |
| JP | 2016-536698 | 11/2016 |
| JP | 2017-500004 | 1/2017 |
| JP | 2017-33046 | 2/2017 |
| WO | WO 2014/041380 A1 | 3/2014 |
| WO | WO 2015/048753 A1 | 4/2015 |
| WO | WO 2015-112619 A1 | 7/2015 |
| WO | WO 2017/053683 | 3/2017 |

OTHER PUBLICATIONS

The COSMIC (Catalogue of Somatic Mutations in Cancer) database and website. S Bamford et al. British Journal of Cancer (2004) 91, pp. 355-358. (Year: 2004).*

Principles of analytical validation of next-generation sequencing based mutational analysis for hematologic neoplasms in a CLIA-certified laboratory. Kanagal-Shamanna R, Singh RR, Routbort MJ, Patel KP, Medeiros LJ, Luthra R. Expert Review of Molecular Diagnostics. Volume 16, pp. 461-472. (Year: 2016).*

Bioinformatics for Clinical Next Generation Sequencing. Gavin R Oliver, Steven N Hart, Eric W Klee. Clinical Chemistry, vol. 61, Issue 1, Jan. 1, 2015, pp. 124-135. (Year: 2015).*

Guidelines for Validation of Next-Generation Sequencing-Based Oncology Panels. Lawrence J Jennings, Maria E Arcila, Christopher Corless, Suzanne Kamel-Reid, Ira M Lubin, John Pfeifer, Robyn L Temple-Smolkin, Karl V Voelkerding, Marina N Nikiforova. J Mol Diagn. May 2017; 19(3): pp. 341-365. (Year: 2017).*

Uwe Baier, Timo Beller, Enno Ohlebusch: Graphical pan-genome analysis with compressed suffix trees and the Burrows-Wheeler transform, Bioinformatics, vol. 32, Issue 4, Feb. 15, 2016, pp. 497-504 (Year: 2016).*

Forbes: ("COSMIC: exploring the world's knowledge of somatic mutations in human cancer", Nucleic Acids Research, 2015, vol. 43 , Database issue D805-D811 (Year: 2015).*

Reporting Letter received from Japanese associate dated Jun. 26, 2019 enclosing Extended European Search Report received in European Application No. 18205386.8 dated Apr. 11, 2019, pp. 1-2.

(56) References Cited

OTHER PUBLICATIONS

Extended European Search Report dated Apr. 11, 2019 received in European Application No. 18205386.8, pp. 3-5.
Office Action in Japanese Application No. 2017-216502, dated Jul. 13, 2021, 8 pages (including English translation), pp. 1-8.
Communication/Office Action received in European Application No. 18 205 386.8 dated Feb. 10, 2021, pp. 1-8.
Chinese Office Action with English Translation, dated Feb. 15, 2023, pp. 1-19, Issued in Chinese patent application No. 201811329017. 6, China National Intellectual Property Administration, Beijing, China.
"Genome Sequencing and Analysis of *E. coli* H001 Strain and *E. coli* V0001 Strain, Hongsheng Zhang (Bioinformatics), Directed by Prof. Jun. Yu, Beijing Institute of Genomics Chinese Academy of Sciences, Apr. 2011".
Notice of Allowance in China Application No. 201811329017.6, including English tranlsation, dated Jul. 7, 2023, 12 pages.

\* cited by examiner

| GENE NAME | GENE ID |
|---|---|
| ... | ... |
| EGFR | aaa |
| BRAF | bbb |
| Ros1 | ccc |
| ... | ... |

121B

| GENE PANEL NAME | GENE PANEL ID | RELATED GENE ID |
|---|---|---|
| ... | ... | ... |
| A Panel | AAA | aaa, bbb, ccc, ... |
| B Panel | BBB | aaa, bbb, ccc, ddd, ... |
| C Panel | CCC | aaa, ccc, ... |
| ... | ... | ... |

121C

| GENE PANEL NAME | GENE |
|---|---|
| LUNG CANCER PANEL | EGFR, ALK, ROS1, ... |
| COLON CANCER PANEL | RAS, APC, ... |
| BREAST CANCER PANEL | BRCA1, BRCA2, ... |
| ... | ... |

| GENE NAME | REARRANGED SEQUENCE ID | LENGTH OF REARRANGED SEQUENCE | LENGTH TO MUTATION SEQUENCE | MUTATION ID | MUTATION SEQUENCE | CHROMOSOME NUMBER | POSITION |
|---|---|---|---|---|---|---|---|
| EGFR | ... | ... | ... | ... | ... | ... | ... |
| | aa | 325 | na | aaaa | a | CHa | pa |
| | bb | 467 | nb | bbbb | b | CHb | pb |
| | cc | 416 | nc | cccc | c | CHc | pc |
| | ... | ... | ... | ... | ... | ... | ... |

122B

| GENE NAME | REFERENCE SEQUENCE ID | GENERATION DATE |
|---|---|---|
| ... | ... | ... |
| BRAF | braf-20170901 | 2017/9/1 |
| EGFR | egfr-20170801 | 2017/8/1 |
| ... | ... | ... |

122C

| REFERENCE SEQUENCE ID | CONNECTION INFORMATION |
|---|---|
| ... | ... |
| braf-20170901 | aa(325), bb(467), cc(416), ... |
| egfr-20170801 | hh(430), ii(481), jj(644), ... |
| ... | ... |

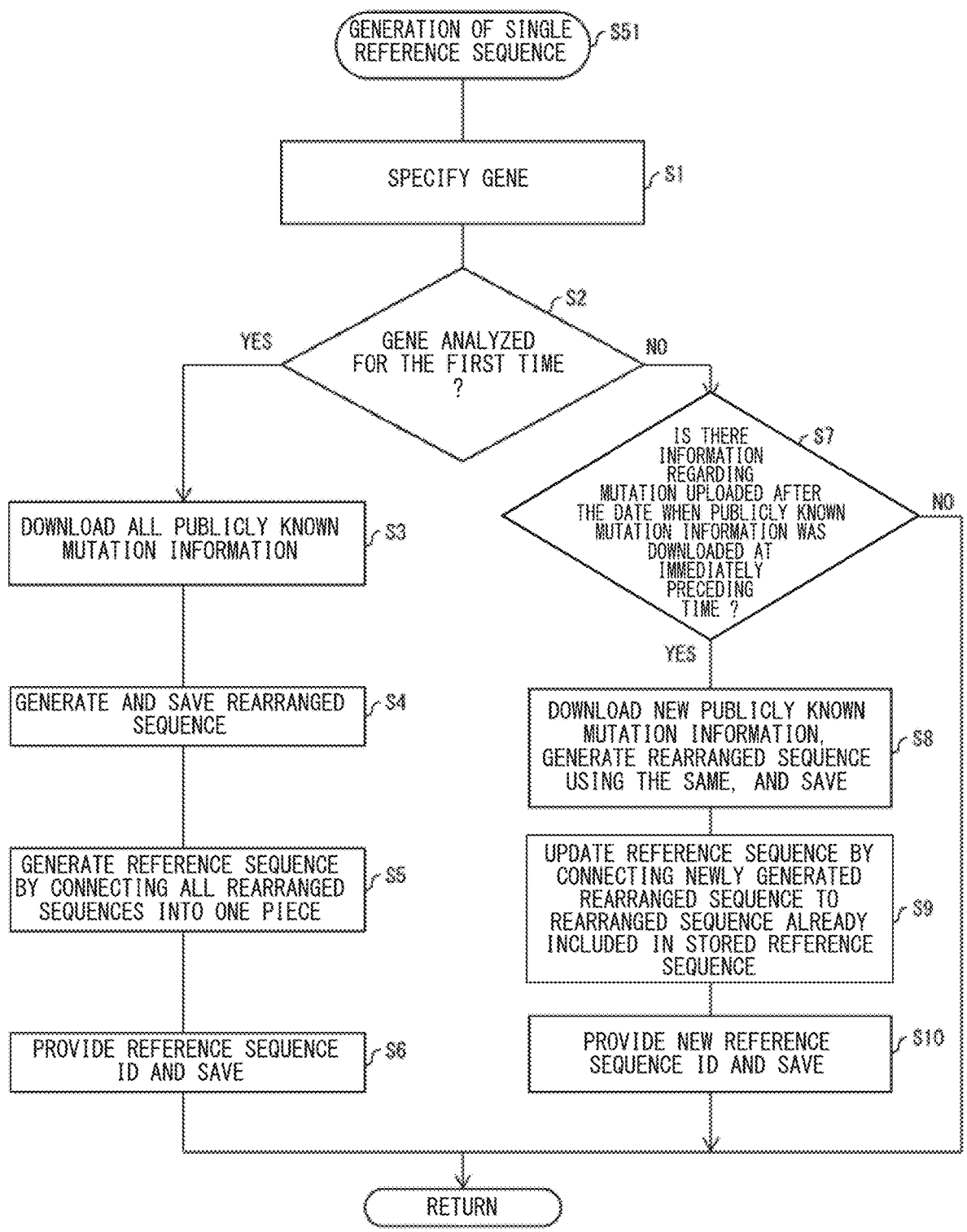

FIG. 10A  FRAGMENTATION OF SAMPLE (DNA)
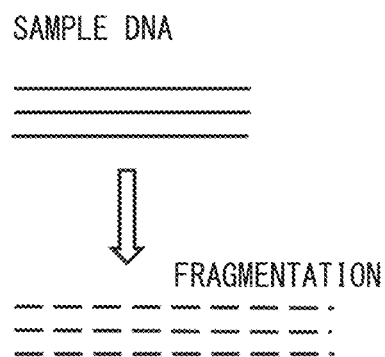
FIG. 10B  PROVISION OF ADAPTER SEQUENCE
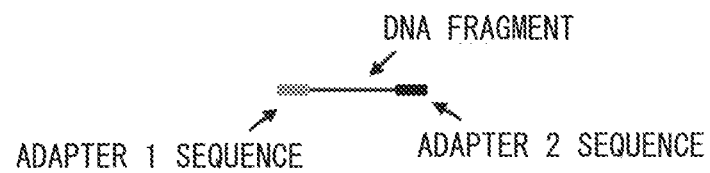
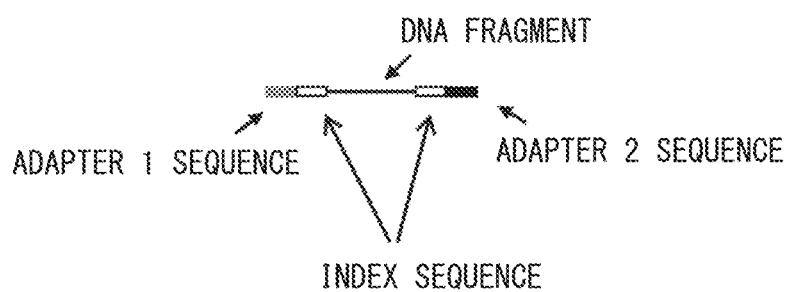

FIG. 12
COLLECT DNA FRAGMENT AS ANALYSIS TARGET
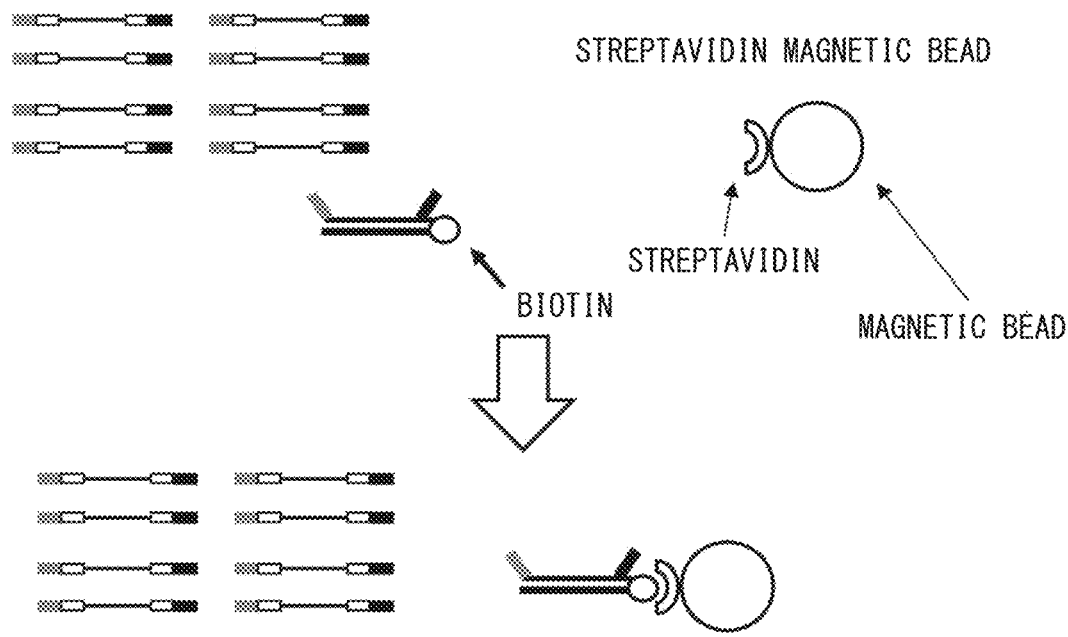
WASH AND COLLECT
WASH AND REMOVE DNA FRAGMENTS THAT WERE NOT HYBRIDIZED
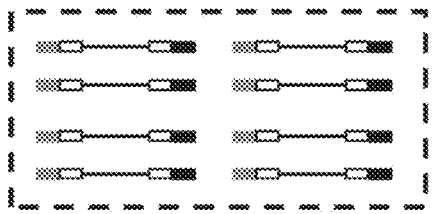
COLLECT HYBRIDIZED DNA FRAGMENTS BY MAGNET
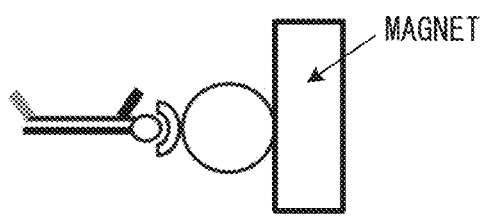

FIG. 17

```
· SEQUENCE NAME: "Read Seq 1"    (SEQ ID NO:1)
· SEQUENCE:       ···GTAAGGCACGTCATA···
· QUALITY SCORE:         ···xxxxxyzxxyzzxxx···
```

FIG. 20

| GENE NAME | CHROMOSOME POSITION | MUTATION |
|---|---|---|
| AKT1 | 14q32.33 | p.E17K |
| BRAF | 7q34 | p.V600E, p.V600K, p.V600, p.V600R, p.K601E, p.D594G, p.G469A, p.D594N, p.V600M, p.V600_K601>E, p.G466V, p.V600D, p.L597R, p.G469V, p.N581S, p.V600L, p.G469R, p.G469E, p.G466E, p.L597Q, p.L597S, p.V600A |
| EGFR | 7p11.2 | p.L858R, p.E746_A750del, p.E746_A750delELREA, p.T790M, p.L861Q, p.G719, p.S768I, p.L747_P753>S, p.G719A, p.L747_T751del, p.L747_A750>P, p.G719S, p.L747_T751delLREAT, p.E746_S752>V, c.3633+294delA, p.V769_D770insASV, p.L747_S752del, p.G719C, p.L747_S752delLREATS, p.G598V, p.A289V, c.3633+293_3633+294delAA, p.L747_P753del, p.D770_N771insSVD, p.E746_T751del, p.L747_T751>P, p.E709K, p.E746_T751>A, p.L833V, p.N158N, p.K745_A750del, p.H773_V774insNPH, p.C797S |
| ... | ... | ... |

FIG. 23A

```
REFERENCE SEQUENCE: · · · GCCATGGACAGAAGGCGCAGGGC · · ·   (SEQ ID NO:2)
READ SEQUENCE R1:          GCCATGGACAGAA                  (SEQ ID NO:3)
READ SEQUENCE R2:          GCCATGCACAGAA                  (SEQ ID NO:4)
```

FIG. 23B

```
REFERENCE SEQUENCE: · · · GCCATGGACAGAAGGCGCAGGGC · · ·   (SEQ ID NO:2)
READ SEQUENCE R3:          GCCATGGACAG**GGCG              (SEQ ID NO:5)
READ SEQUENCE R4:          GCCATGGACAGAAGGCG              (SEQ ID NO:6)
                                  ⏜
                                 CGGT
```

FIG. 24

- POSITION INFORMATION: POSITION INFORMATION ON REFERENCE GENOME.
  FOR EXAMPLE, SPECIFIED BY CHROMOSOME NUMBER AND POSITION ON THE CHROMOSOME
- REFERENCE BASE: REFERENCE BASE (A, T, C, G, etc.) IN THE POSITION INFORMATION
- MUTATION BASE: BASE OF REFERENCE BASE AFTER MUTATION

| CHROM | POS | REF | ALT | |
|---|---|---|---|---|
| 20 | 3 | C | G | |
| 21 | 4 | C | CTAG | ← EXAMPLE OF INSERTION MUTATION |
| 19 | 10 | TCG | T | ← EXAMPLE OF DELETION MUTATION |
| 2 | 321681 | G | G]17:198982] | ← REVERSE COMPLEMENT SEQUENCE OF SEQUENCE EXTENDING AT LEFT OF 198982 POSITION OF CHROMOSOME 17 IS BOUND AFTER "G" |
| 2 | 321682 | T | ]13:123456]T | ← SEQUENCE AT LEFT OF 123456 POSITION OF CHROMOSOME 13 IS BOUND BEFORE "T" |
| 13 | 123456 | C | C[2:321682[ | ← SEQUENCE AT RIGHT OF 321682 POSITION OF CHROMOSOME 2 IS BOUND AFTER "C" |
| 13 | 123457 | A | [17:198983[A | ← REVERSE COMPLEMENT SEQUENCE OF SEQUENCE EXTENDING AT RIGHT OF 198983 POSITION OF CHROMOSOME 17 IS BOUND AFTER "C" |

FIG. 25

| MUTATION ID | CHROM | POS | REF | ALT | Annotation |
|---|---|---|---|---|---|
| #1 | 20 | 3 | C | G | abc |
| #2 | 19 | 4 | A | T | xyz |
| #3 | xx | yy | C | G | EGFR L858R |
| #4 | aa | bb | T | A | BRAF V600E |
| ... | ... | ... | ... | ... | ... |
| #xx | abc | ABC | G | G]p] | ALK-EML4 FUSION |
| #yy | xyz | XYZ | T | ]p]T | ROS1-CD74 FUSION |
| ... | ... | ... | ... | ... | ... |

- MUTATION ID: IDENTIFIER FOR IDENTIFYING MUTATION
- MUTATION POSITION INFORMATION:
  - CHROM: CHROMOSOME NUMBER
  - POS: POSITION AT CHROMOSOME NUMBER
- REF: WILD TYPE BASE
- ALT: BASE AFTER MUTATION
- ANNOTATION: INFORMATION REGARDING MUTATION. EXAMPLE) EGFR C2573G, EGFR L858R

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: an artificial sequence reference gene

<400> SEQUENCE: 1
gtaaggcacg tcata                                                        15

<210> SEQ ID NO 2
<211> LENGTH: 23
<212> TYPE: DNA
<213> ORGANISM: Artificial Sequence
<220> FEATURE:
<223> OTHER INFORMATION: an artificial sequence reference gene

<400> SEQUENCE: 2
gccatggaca gaaggcgcag ggc                                               23

<210> SEQ ID NO 3
<211> LENGTH: 13
<212> TYPE: DNA
<213> ORGANISM: Artificial Sequence
<220> FEATURE:
<223> OTHER INFORMATION: an artificial read sequence

<400> SEQUENCE: 3
gccatggaca gaa                                                          13

<210> SEQ ID NO 4
<211> LENGTH: 13
<212> TYPE: DNA
<213> ORGANISM: Artificial Sequence
<220> FEATURE:
<223> OTHER INFORMATION: an artificial read sequence

<400> SEQUENCE: 4
gccatgcaca gaa                                                          13

<210> SEQ ID NO 5
<211> LENGTH: 15
```

```
<212> TYPE: DNA
<213> ORGANISM: Artificial Sequence
<220> FEATURE:
<223> OTHER INFORMATION: an artificial read sequence
<220> FEATURE:
<221> NAME/KEY: misc_feature
<222> LOCATION: (11)..(12)
<223> OTHER INFORMATION: deletion of 2 bases

<400> SEQUENCE: 5
gccatggaca gggcg                                                        15

<210> SEQ ID NO 6
<211> LENGTH: 17
<212> TYPE: DNA
<213> ORGANISM: Artificial Sequence
<220> FEATURE:
<223> OTHER INFORMATION: an artificial read sequence

<400> SEQUENCE: 6
gccatggaca gaaggcg                                                      17

<210> SEQ ID NO 7
<211> LENGTH: 48
<212> TYPE: DNA
<213> ORGANISM: Artificial Sequence
<220> FEATURE:
<223> OTHER INFORMATION: an artificial reference sequence gene
<220> FEATURE:
<221> NAME/KEY: misc_feature
<222> LOCATION: (11)..(12)
<223> OTHER INFORMATION: deletion of 2 bases

<400> SEQUENCE: 7
gccatggaca gggcgcaggg cgccatggac agcggtaagg cgcagggc                    48

<210> SEQ ID NO 8
<211> LENGTH: 21
<212> TYPE: DNA
<213> ORGANISM: Artificial Sequence
<220> FEATURE:
<223> OTHER INFORMATION: an artificial read sequence

<400> SEQUENCE: 8
gccatggaca gcggtaaggc g                                                 21
```

SEQUENCE ANALYSIS METHOD, SEQUENCE ANALYSIS APPARATUS, REFERENCE SEQUENCE GENERATION METHOD, REFERENCE SEQUENCE GENERATION APPARATUS, PROGRAM, AND STORAGE MEDIUM

RELATED APPLICATIONS

This application claims priority from prior Japanese Patent Application No. 2017-216502, filed on Nov. 9, 2017, entitled "Sequence Analysis Method, Sequence Analysis Apparatus, Reference Sequence Generation Method, Reference Sequence Generation Apparatus, Program, and Storage Medium", the entire content of which is incorporated herein by reference.

BACKGROUND OF THE INVENTION

1. Field of the Invention

The present invention relates to a sequence analysis method, a sequence analysis apparatus, a sequence analysis program, and a storage medium.

2. Description of the Related Art

Conventionally, gene sequence analysis has been utilized as an important tool in basic study, clinical study, and medical care, in recent years, next-generation sequencers (NGS) have appeared and it has become possible to obtain a large amount of gene sequence information comprehensively and at high speed. Accordingly, gene sequence analysis has been utilized in broader fields.

One example of technologies that utilizes gene sequence analysis is target sequencing. The target sequencing is a technique of determining base sequences only with respect to a target region in the entire genome sequence. The target sequencing enables analysis of only gene sequences of a target region that includes hereditary-disorder-related genes, cancer related genes, and the like, and acquisition of highly useful analysis results at low sequencing cost.

For example, gene panels, with which a plurality of mutations occurring in genes related to a specific disease can be analyzed in detail and at high-throughput by use of a next-generation sequencer, are recognized as a useful tool for diagnosing the disease.

Japanese Translation of PCT International Application Publication No. 2015-536661 discloses a method for quickly and efficiently mapping read sequences obtained through target sequencing. In the method described in Japanese Translation of PCT International Application Publication No. 2015-536661, read sequences are mapped with respect to a reference sequence not of the entire genome but of a target region for which sequence reading is performed. Thus, the calculation efficiency is improved. In addition, in order to prevent a read sequence similar to the sequence of a target region being erroneously mapped on the target region, a reference sequence of an alternate region that is similar to a target region of a reference genome is also used in alignment of read sequences. The degree of agreement between the target region and each read sequence and the degree of agreement between the alternate region and the each read sequence are determined, and when the read sequence is more similar to the target region compared with the alternate region, the read sequence is mapped on the target region.

SUMMARY OF THE INVENTION

The scope of the present invention is defined solely by the appended claims, and is not affected to any degree by the statements within this summary.

There are cases where polymorphism, mutation, methylation, and the like occur in the sequences of genes that are to be analyzed (hereinafter, also referred to as analysis targets). For example, in a case where a mutation such as deletion or insertion has occurred, if a reference sequence of a target region that does not include any mutation is used, alignment accuracy could be reduced.

In order to solve the above problem, a sequence analysis method according to one aspect of the present invention is a method for analyzing nucleic acid sequence, the method including: obtaining a plurality of read sequences read from the nucleic acid sequence; and determining the nucleic acid sequence by aligning the plurality of read sequences with reference to a single reference sequence, wherein the reference sequence comprises at least a first rearrangement sequence and a second rearrangement sequence that is different from the first rearrangement sequence.

According to the aspect of present invention, a plurality of read sequences read from the nucleic acid sequence are aligned with reference to a single reference sequence that comprises at least a first rearrangement sequence and a second rearrangement sequence that is different from the first rearrangement sequence. Accordingly, even when polymorphism, mutation, methylation, and the like have occurred in the sequence of the analysis target gene, the read sequences can be more accurately mapped.

Even when the number of rearrangement sequences has changed, since the read sequences are aligned with reference to a single reference sequence that comprises a plurality of rearrangement sequences, the number of the reference sequence that is used in alignment does not change. Therefore, information regarding a new mutation can be easily reflected in the alignment of the read sequences.

"Read sequence" means a polynucleotide sequence obtained by sequencing. "Rearrangement sequence" is a partial sequence or a complete sequence of a wild type exon that includes at least one of known polymorphism, known mutation, known methylation that have occurred in the wild type exon or the like included in a genome sequence.

"Reference sequence" is a sequence with respect to which each read sequence is mapped in order to determine which region on the gene the read sequence corresponds to, which mutation on the gene the read sequence corresponds to, and the like. For each gene to be analyzed, as the reference sequence, (1) a wild-type reference sequence which is a partial sequence or a complete sequence of a wild type exon, and (2) a single reference sequence obtained by connecting, into one piece, rearrangement sequences which each include known polymorphism or mutation from the wild type exon sequence, can be used. In a case where bisulfite sequencing is performed, a sequence in which unmethylated cytosine is converted to uracil through bisulfite treatment can be used as a wild type sequence, and a sequence in which cytosine remains unconverted can be used as a rearrangement sequence. "Mapping" means a process of aligning each read sequence to a region having the highest matching rate between the read sequence and a base sequence in the reference sequence that is used.

"Single reference sequence" is a sequence generated, for each gene to be analysis target, by connecting two or more rearrangement sequences regarding the gene as the analysis target, into one piece. The single reference sequence is used as the only one reference sequence that comprises rearrangement sequences, when each read sequence is mapped.

Bisulfite sequencing is one technique for analyzing methylation of DNA. There are cases where cytosine among the four bases forming DNA is methylated to become methylated cytosine. This is called methylation of DNA. Bisulfite sequencing is a sequencing method that is used in order to detect the methylated cytosine. In bisulfite sequencing, DNA contained in a sample is treated by bisulfite, whereby unmethylated cytosine of DNA undergoes base substitution to be replaced with uracil. Meanwhile, methylated cytosine does not undergo base substitution and is not replaced with uracil even through bisulfite treatment. Sequence analysis is performed after the bisulfite treatment, and cytosine that has not been replaced with uracil is determined. Accordingly, cytosine methylated in the sample DNA can be determined.

"Mutation" means at least one of mutations such as polymorphism, substitution, InDel, and the like of a gene. "InDel (Insertion and/or Deletion)" means a mutation that includes insertion, deletion, or both of insertion and deletion. "Polymorphism" of a gene includes SNV (single nucleotide variant, single nucleotide polymorphism), VNTR (variable nucleotide of tandem repeat, repeat sequence polymorphism), STRP (short tandem repeat polymorphism, microsatellite polymorphism), and the like.

The first rearrangement sequence may comprise at least one of polymorphism, mutation, and methylation, and the second rearrangement sequence comprises at least one of polymorphism, mutation, and methylation.

The polymorphism may be any one of repeat sequence polymorphism, microsatellite, and single nucleotide polymorphism, and the mutation may be any one of substitution, deletion, and insertion.

The determining may comprise comparing the read sequence with the reference sequence, and mapping the read sequence to a region on the reference sequence, that has a highest matching rate between the read sequence and the reference sequence.

The sequence analysis method may further comprise generating the reference sequence that comprises the first rearrangement sequence and the second rearrangement sequence.

The sequence analysis method, in the determining the nucleic acid sequence, may use the reference sequence comprising the first rearrangement sequence and the second rearrangement sequence which are generated on the basis of known mutation information obtained from a mutation information database (3, 3a).

"Mutation information" may include known mutation information which is publicly known mutation information and mutation information that has not been made public. "Publicly known mutation information" is not limited to information regarding mutation but may also include information regarding polymorphism and methylation. Similar to publicly known mutation information, known mutation information may include information regarding mutation, polymorphism, and methylation.

The known mutation information and information indicating when the known mutation information was obtained may be associated with each other in the mutation information database (3, 3a).

The sequence analysis method may further comprise adding a third arrangement sequence so as to be included in the reference sequence.

The sequence analysis method may further comprise adding a third arrangement sequence so as to be connected with at least one of the first rearrangement sequence and the second rearrangement sequence.

In the generating of the reference sequence, when known mutation information that is different from known mutation information used in generation of the first rearranged sequence and the second rearranged sequence has been newly stored in the mutation information database (3, 3a), the generating of the reference sequence may comprise generating on the basis of a third rearranged sequence generated on the basis of the newly stored known mutation information, the reference sequence including the first rearranged sequence, the second rearranged sequence, and the third rearranged sequence.

In the generating of the reference sequence, when known mutation information that is different from known mutation information used in generation of the first rearranged sequence and the second rearranged sequence has been newly stored in the mutation information database (3, 3a), the generating of the reference sequence may comprise generating the reference sequence, by connecting, on the basis of a third rearranged sequence generated on the basis of the newly stored known mutation information, the third rearranged sequence to the first rearranged sequence or to the second rearranged sequence.

The sequence analysis method may further comprise providing each of known mutation information stored in the mutation information database (3, 3a) with individual identification information, and generating the first rearrangement sequence, the second rearrangement sequence, and the third rearrangement sequence on the basis of known mutation information respectively provided with different identification information.

The first rearrangement sequence may be a partial sequence or a complete sequence of an exon or intron that has at least one of polymorphism, mutation, or methylation, and the second rearrangement sequence may be a partial sequence or a complete sequence of an exon or intron that has at least one of polymorphism, mutation, or methylation.

The obtaining may comprise obtaining the plurality of read sequences by reading the nucleic acid sequence collected with a bait.

The sequence analysis method may further comprise reading the plurality of read sequences by using oligo DNA immobilized on a surface of a member. Examples of a member to be used for reading the nucleic acid sequence include flow cells and the like shown in FIG. 13, FIG. 14, and the like.

The determining may comprise comparing the plurality of read sequences with a wild-type reference sequence and the single reference sequence.

The reference sequence may comprise the first rearrangement sequence for a gene to be analyzed and a second rearrangement sequence for another gene to be analyzed.

The sequence analysis method may further comprise reading the plurality of read sequences by use of a next-generation sequencer.

The sequence analysis method may further comprise obtaining a plurality of single reference sequences for each gene to be analyzed, wherein the determining comprises aligning the plurality of read sequences with reference to each of the plurality of single reference sequence.

In order to solve the above problem, a sequence analysis apparatus according to another aspect of the present invention is a sequence analysis apparatus (1) comprising: a read sequence information obtaining unit (111) configured to obtain a plurality of read sequences read from the nucleic acid sequence; and a sequence determination unit (113)

configured to determine the nucleic acid sequence by aligning the plurality of read sequences with reference to a single reference sequence, wherein the reference sequence comprises at least a first rearrangement sequence and a second rearrangement sequence that is different from the first rearrangement sequence.

According to the aspect of present invention, a plurality of read sequences read from nucleic acid sequence are aligned with reference to a single reference sequence that comprises a plurality of rearrangement sequences. Accordingly, even when polymorphism, mutation, methylation, and the like have occurred in the sequence of the analysis target gene, the read sequences can be more accurately mapped. Since information regarding a new mutation can be uploaded in the single reference sequence, even when the number of rearrangement sequences has changed, the read sequences can be aligned with reference to the single reference sequence. This also provides an effect that the routine of the analysis program need not be modified.

The sequence determination unit (113) may compare the read sequence with the reference sequence and determine a region, on the reference sequence, that has a highest matching rate between the read sequence and the reference sequence.

The sequence analysis apparatus may further include a reference sequence generation unit (115) configured to generate the reference sequence that includes the first rearrangement sequence and the second rearrangement sequence.

The sequence analysis apparatus may further comprise a reference sequence management unit (112) may be configured to obtain, from a mutation information database (3, 3a), known mutation information to be used in generation of the first rearrangement sequence and the second rearrangement sequence.

The reference sequence generation unit (115) may generate the reference sequence that includes the first rearrangement sequence, the second rearrangement sequence, and a third rearrangement sequence generated on the basis of known mutation information that is different from known mutation information used in generation of the first rearrangement sequence and the second rearrangement sequence.

The reference sequence generation unit (115) may generate the reference sequence by connecting a third rearrangement sequence to the first rearrangement sequence or to the second rearrangement sequence, the third rearrangement sequence being generated on the basis of known mutation information that is different from known mutation information used in generation of the first rearrangement sequence and the second rearrangement sequence.

Each of known mutation information stored in the mutation information database (3, 3a) may be provided with individual identification information, and the reference sequence management unit (112) may generate the first rearrangement sequence, the second rearrangement sequence, and the third rearrangement sequence on the basis of pieces of known mutation information respectively provided with different pieces of identification information.

The sequence determination unit (113) may compare each of the plurality of read sequences with a wild-type reference sequence and the reference sequence.

The sequence analysis apparatus may further include an output unit (14) configured to output information regarding which of the reference sequence or the wild-type reference sequence matches the nucleic acid sequence determined by the sequence determination unit (113).

In order to solve the above problem, a reference sequence generation method according to another aspect of present invention is a reference sequence generation method comprising: obtaining a first rearrangement sequence and a second rearrangement sequence; and generating a reference sequence in which the first rearrangement sequence and the second rearrangement sequence are connected in one piece.

According to the above aspect of present invention, the single reference sequence is generated by connecting into one piece the first rearrangement sequence and the second rearrangement sequence. If the nucleic acid sequence of the read sequence is determined by performing aligning using the single reference sequence generated in this manner, a similar effect to that according to the sequence analysis method above is exhibited.

Each of the first rearrangement sequence and the second rearrangement sequence may be a sequence that includes at least one of polymorphism, mutation, and methylation.

The polymorphism may be any one of repeat sequence polymorphism, microsatellite, and single nucleotide polymorphism, and the mutation may be any one of substitution, deletion, and insertion.

Each of the first rearrangement sequence and the second rearrangement sequence may be generated on the basis of information obtained from a mutation information database (3, 3a).

Known mutation information and information indicating a date and a time at which the known mutation information was stored in the mutation information database (3, 3a) may be associated with each other in the mutation information database (3, 3a).

In the generating of the reference sequence, when known mutation information that is different from known mutation information used in generation of the first rearrangement sequence and the second rearrangement sequence has been newly stored in the mutation information database (3, 3a), the reference sequence is generated on the basis of a third rearrangement sequence generated on the basis of the newly stored known mutation information, the reference sequence including the first rearrangement sequence, the second rearrangement sequence, and the third rearrangement sequence.

In the generating of the reference sequence, when known mutation information that is different from known mutation information used in generation of the first rearrangement sequence and the second rearrangement sequence has been newly stored in the mutation information database (3, 3a), the reference sequence may be generated on the basis of a third rearrangement sequence generated on the basis of the newly stored known mutation information, the reference sequence being obtained by connecting the third rearrangement sequence to the first rearrangement sequence or to the second rearrangement sequence.

Each of the first rearrangement sequence and the second rearrangement sequence may include polymorphism, mutation, or methylation, and each of the first rearrangement sequence and the second rearrangement sequence may be a partial sequence or a complete sequence of an exon that has the polymorphism, the mutation, or the methylation.

In order to solve the above problem, a reference sequence generation apparatus according to another aspect of the present invention is a reference sequence generation apparatus configured to generate a reference sequence to be used for determining a nucleic acid sequence of a read sequence read by a sequencer (2), the reference sequence generation apparatus including: a reference sequence management unit configured to obtain a first rearrangement sequence and a second rearrangement sequence; and a reference sequence generation unit configured to generate a reference sequence in which the first rearrangement sequence and the second rearrangement sequence are connected in one piece.

According to the above aspect of present invention, even when the number of rearrangement sequences has changed, the number of the reference sequence that is used for aligning the read sequences does not change. Therefore, information regarding a new mutation can be easily reflected in the alignment of the read sequences.

The sequence analysis apparatus (1) according to each aspect of the present invention may be realized by a computer. In addition, the program for making a computer realize the functions of the sequence analysis apparatus (1) and a computer-readable storage medium having the program stored therein is also included in the scope of the present invention.

According to present invention, even when polymorphism, mutation, methylation, and the like have occurred in the sequence of an analysis target gene, read sequences can be more accurately and efficiently mapped.

BRIEF DESCRIPTION OF THE DRAWINGS

FIG. 5 is a diagram showing an example of a data structure of a gene panel information database;

FIG. 6 is a diagram showing an example of a data structure of a reference sequence database;

FIG. 8 is a flow chart describing one example of the flow of a process of generating and updating a reference sequence;

FIG. 10A is a diagram describing an example of a step of fragmenting a sample;

FIG. 10B is a diagram describing an example of a step of providing an index sequence and adapter sequences;

FIG. 12 is a diagram describing one example of a step of collecting DNA fragments as analysis targets;

FIG. 17 is a diagram showing one example of a file format of read sequence information;

FIG. 20 is a diagram showing an example of known mutations incorporated into reference sequences (that do not show wild type sequences) included in the reference sequence database;

FIG. 23A is a diagram showing one example of score calculation;

FIG. 23B is a diagram showing another example of the score calculation;

FIG. 24 is a diagram showing one example of a format of a result file generated by a mutation identification unit;

FIG. 25 is a diagram showing one example of a structure of a mutation database;

FIG. 26 is a diagram showing an example of details of a structure of information regarding a mutation in the mutation database;

DETAILED DESCRIPTION OF THE PREFERRED EMBODIMENTS

In the present embodiment, a sample that contains DNA is fragmented so as to have a length at which a sequencer reads a sequence, the base sequence of each DNA fragment is read by the sequencer, and read sequences having been read are mapped on a single reference sequence obtained by connecting, into one piece, a plurality of rearrangement sequences including mutations, whereby alignment is performed.

In a case where a single reference sequence obtained by connecting a plurality of rearrangement sequences into one piece is not used, if a read sequence is to be mapped through comparison of the read sequence with two or more rearrangement sequences, it is common that, firstly, a read sequence as a mapping target is compared with a wild-type reference sequence, one rearrangement sequence 1 is read out, and the read sequence and the rearrangement sequence 1 are compared with each other. Next, a rearrangement sequence 2 is read out, and the read sequence and the rearrangement sequence 2 are compared with each other. In this method, it is necessary to repeat the process of reading out rearrangement sequences one by one and comparing the read sequence with each rearrangement sequence until the read sequence is compared with all of the rearrangement sequences.

However, in recent years, there are increasing concerns on mutations that occur in genes, and it is considered that information regarding mutations is continued to be added and accumulated globally, in association with progress of research and development. Therefore, when alignment of read sequences is performed, rearrangement sequences that include known mutations are not fixed in number, but gradually increased or sometimes decreased.

In the above-described general method in which rearrangement sequences are read out one by one to be compared with the read sequence, in a case where information regarding known mutations has been uploaded or deleted and thus the number of rearrangement sequences that include known mutations has changed, it is necessary to modify a program routine for adding or deleting rearrangement sequences that should be read out.

Meanwhile, in the present embodiment, after a read sequence is compared with a wild-type reference sequence, the read sequence is compared with a single reference sequence obtained by connecting a plurality of rearrangement sequences into one piece, and then, the position on the reference sequence at which the matching rate with the read sequence satisfies a predetermined level is identified.

Thus, the present embodiment has an advantage that, since a reference sequence obtained by connecting a plurality of rearrangement sequences into one piece is used, even when the number of rearrangement sequences has changed, information regarding a new mutation can be reflected in the single reference sequence, and thus, the program routine need not be modified.

Embodiments of the present disclosure are described in detail.

Figure 1:
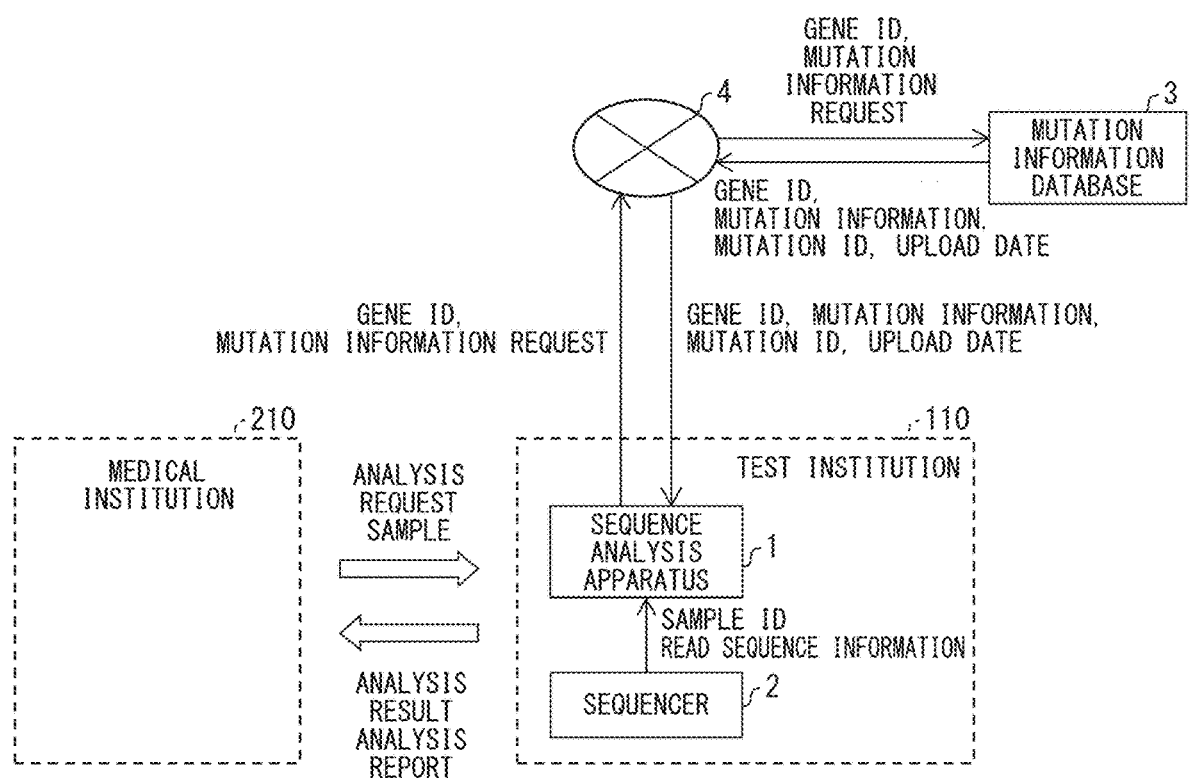
FIG. 1 is a diagram showing an application example of a sequence analysis apparatus.

In the following, an example case in which a sequence analysis apparatus 1 according to an embodiment of the present disclosure is installed in a test institution 110 is described. FIG. 1 is a diagram showing an application example of the sequence analysis apparatus 1.

(Test Institution 110)

The test institution 110 tests/analyzes samples provided from one or plurality of medical institutions 210 and provides analysis results to the medical institutions 210. In the test institution 110, as shown in FIG. 1, one or a plurality of sequencers 2, the sequence analysis apparatus 1, and the like are installed.

In the test institution 110 shown in FIG. 1, in response to an analysis request from the medical institution 210, a sample is analyzed and an analysis report is created on the basis of the analysis result. Here, a "sample" is used synonymously with a specimen or a preparation in this field, A "sample" is intended to mean any specimen and preparation obtained from a biological material (for example, individual, blood, body fluid, urine, cell strain, cultured tissue, or tissue section) as a supply source.

(Mutation Information Database 3)

A mutation information database 3 shown in FIG. 1 is a public sequence information database, a publicly known mutation information database, or the like which is managed outside the test institution 110. Examples of the public sequence information database include NCBI RefSeq (web page: www.ncbi.nlm.nih.gov/refseq/), NCBI GenBank (web page: www.ncbi.nlm.nih.gov/genbank/), and UCSC Genome Browser. Examples of the publicly known mutation information database include COSMIC database (web page: www.sanger.ac.uk/genetics/CGP/cosmic/), ClinVar database (web page: www.ncbi.nlm.nih.gov/clinvar/), and dbSNP (web page: www.ncbi.nlm.nih.gov/SNP/). The mutation information database 3 may be a publicly known mutation information database that includes frequency information according to the race or the type of animal species, with regard to publicly known mutations. Examples of the publicly known mutation information database having such information include HapMap Genome Browser release #28, Human Genetic Variation Browser (web page: www.genome.med.kyoto-u.ac.jp/SnpDB/index.html) and 1000 Genomes (web page: www.1000genomes.org/). From these databases, for example, mutation frequency information and the like of Japanese people can be obtained.

(Sequencer 2)

The sequencer 2 is an analysis apparatus that is used in order to read the base sequences of genes contained in a sample. For example, preferably, the sequencer 2 is a next-generation sequencer that can read a large amount of base sequences of DNA fragments simultaneously and in a parallel manner. The next-generation sequencer is one of base sequence analysis apparatuses which have been developed in recent years. The next-generation sequencer has a significantly improved analysis capability by performing, in a flow cell, parallel processing of a large amount of single DNA molecules or DNA templates that have been clonally amplified.

Examples of a sequencing technology applicable to the sequencer 2 include sequencing technologies that can obtain a large number of read sequences per run, such as ionic semiconductor sequencing, pyrosequencing, sequencing-by-synthesis using a reversible dye terminator, sequencing-by-ligation, and sequencing by use of probe ligation of oligonucleotide.

A sequencing primer to be used in sequencing is not limited in particular, and is set as appropriate on the basis of a sequence that is suitable for amplifying a target region. Also with respect to reagents to be used in sequencing, suitable reagents may be selected in accordance with the sequencing technology and the sequencer 2 to be used.

(Configuration of Sequence Analysis Apparatus 1)

The sequence analysis apparatus 1 is an apparatus that obtains a plurality of read sequences read from nucleic acid sequence, and that aligns each read sequence with reference to a single reference sequence that includes at least a first rearrangement sequence and a second rearrangement sequence, thereby determining the nucleic acid sequence.

Figure 2:
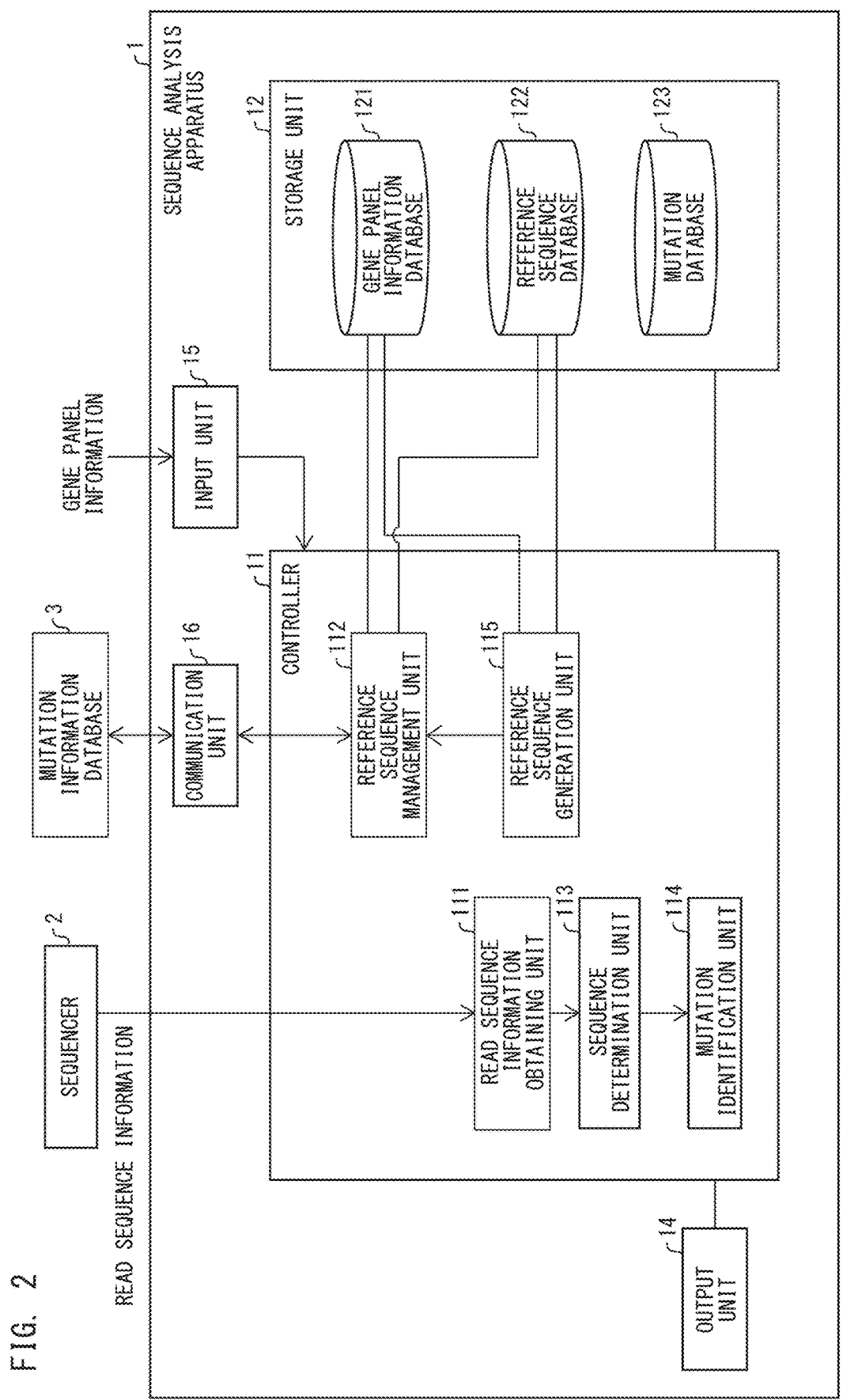
FIG. 2 is a function block diagram showing one example of the sequence analysis apparatus.

The sequence analysis apparatus 1 shown in FIG. 2 includes: a controller 11 which comprehensively controls units of the sequence analysis apparatus 1; a storage unit 12 which has stored therein various types of data that are used by the controller 11; an output unit 14; an input unit 15; and a communication unit 16. The controller 11 is a processor such as a CPU. The controller 11 includes a read sequence information obtaining unit 111, a sequence determination unit 113, a mutation identification unit 114, a reference sequence management unit 112, and a reference sequence generation unit 115. The storage unit 12 is a hard disk drive or the like. The storage unit 12 has stored therein a gene panel information database 121, a reference sequence database 122, and a mutation database 123. The storage unit 12 also has stored therein a program for sequence analysis, a program for generating a single reference sequence, and the like. The output unit 14 includes a display, a printer, a speaker, and the like. The input unit 15 includes a keyboard, a mouse, a touch sensor, and the like. Alternatively, an apparatus may be used that has both of the functions of an input unit and an output unit, such as a touch panel in which a touch sensor and a display are integrated. The communication unit 16 is an interface through which the controller 11 performs communication with an external apparatus.

Figure 3:
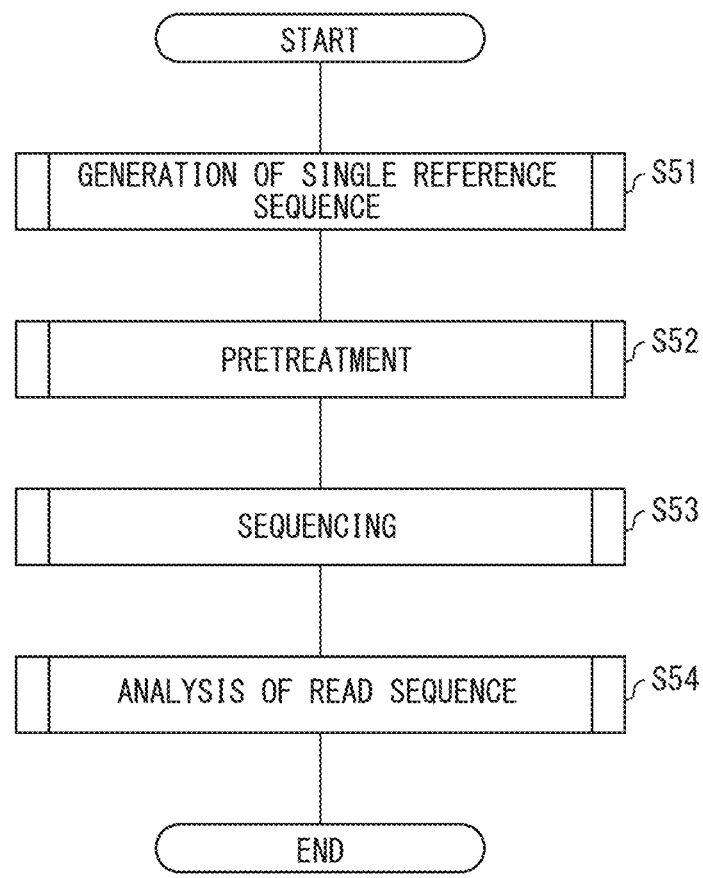
FIG. 3 is a flow chart showing the flow of a process of a test performed in a test institution.

FIG. 3 is a flow chart showing the flow of a process of a test performed in the test institution 110 when an analysis request has been received from the medical institution 210.

First, in the test institution 110, a process of generating a single reference sequence to be used in sequence analysis is performed (step S51).

(Step S51: Process of Generating Single Reference Sequence)

Figure 4:
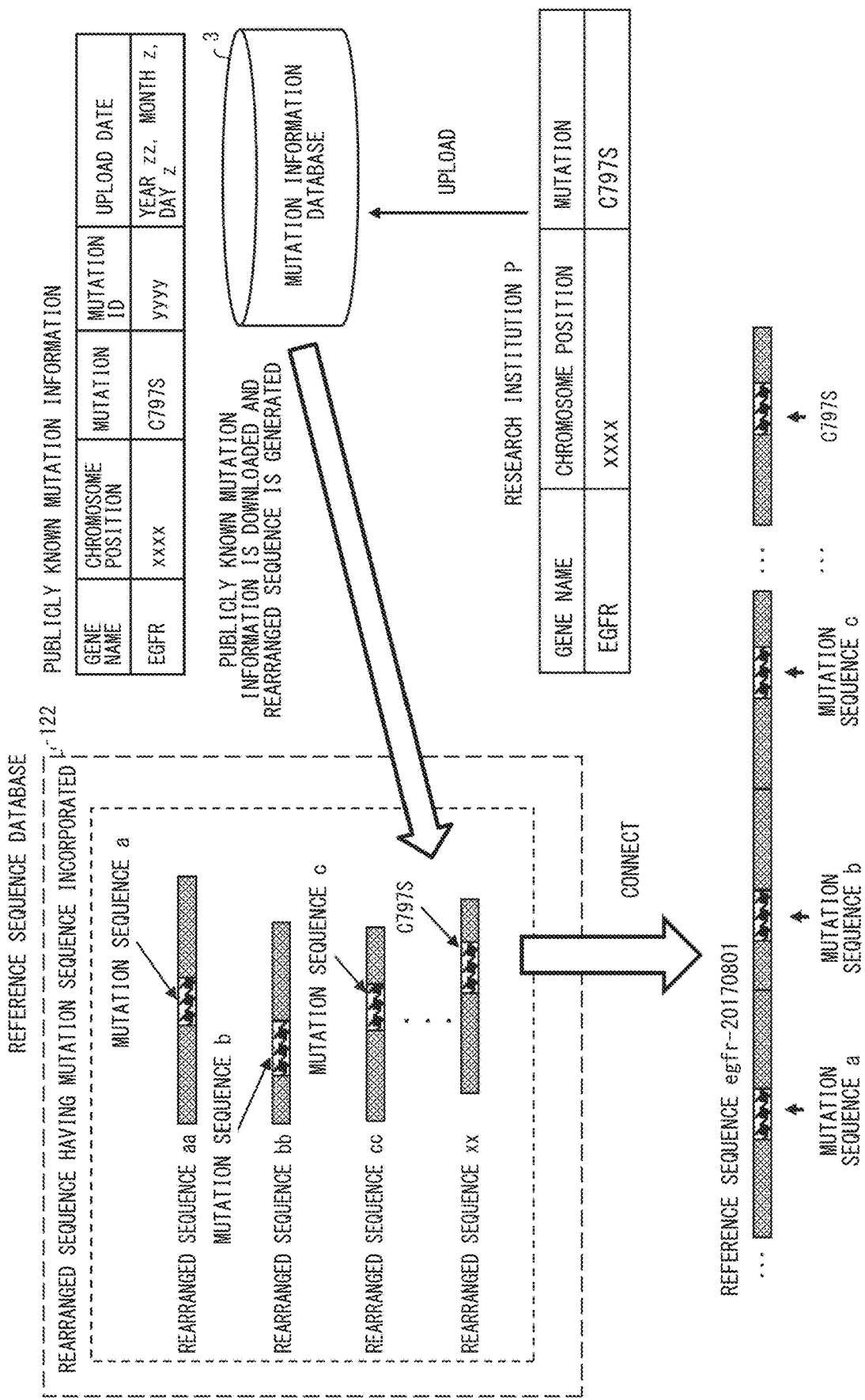
FIG. 4 is a conceptual diagram describing one example of a method for generating a reference sequence by use of publicly known mutation information downloaded from an external mutation information database.

The process of step S51 is performed by the reference sequence management unit 112 and the reference sequence generation unit 115 of the controller 11. FIG. 4 is a conceptual diagram describing one example of a method for generating a reference sequence by use of publicly known mutation information downloaded from an external mutation information database 3.

FIG. 4 shows an example case in which information regarding a mutation "C797S" that has occurred in gene "EGFR" at the chromosome position "xxxx" has been newly uploaded from a research institution P to the external mutation information database 3, and has been stored in the mutation information database 3. The information uploaded from the research institution P and regarding the mutation "C797S" that has occurred at the chromosome position "xxxx" of the gene having the gene name "EGFR" is associated with a mutation ID "yyyy", the upload date "year zz, month z, day z", and the like in the external mutation information database 3, and is registered as publicly known mutation information in the external mutation information database 3. The mutation illustrated here as newly uploaded information is a mutation in which the 797th amino acid residue of protein "EGFR" which is a gene product obtained through transcription/translation according to gene "EGFR" has been substituted from cysteine to serine. Not limited to such a mutation, information regarding polymorphism, mutation, methylation, and the like may be collected and stored in the external mutation information database 3.

The reference sequence management unit 112 transmits a mutation information request to the mutation information database 3, and downloads publicly known mutation information from the mutation information database 3. The reference sequence management unit 112 may be configured to download only publicly known mutation information that has been uploaded to the mutation information database 3 on and after the day on which the reference sequence management unit 112 downloaded publicly known mutation information at the immediately preceding time. According to this embodiment, for example, in a case where the reference sequence management unit 112 downloaded publicly known mutation information from the mutation information database 3 also before "year zz, month z, day z", the reference sequence management unit 112 does not download the publicly known mutation information that was downloaded at the immediately preceding time. In FIG. 4, in a case where the reference sequence management unit 112 downloaded publicly known mutation information from the mutation information database 3 on the previous day of "year zz, month z, day z" and transmitted a mutation information request also on "year zz, month z, day z", the reference sequence management unit 112 may download only the information regarding the mutation "C797S" under the gene name "EGFR" which was uploaded on "year zz, month z, day z" and newly registered as publicly known mutation information.

The reference sequence management unit 112 may be configured to download publicly known mutation information about all the analysis target genes of the sequence analysis apparatus 1 periodically (for example, once a month, once a week, or once in two days) from the mutation information database 3. Alternatively, with respect to one or a plurality of analysis target genes of a gene panel associated with a gene panel name or genes that correspond to gene names or the like inputted through the input unit 15 by a user who uses the sequence analysis apparatus 1, publicly known mutation information may be downloaded in accordance with an instruction from the user. In this case, the reference sequence management unit 112 refers to the gene panel information database 121 and determines genes of which publicly known mutation information should be downloaded. In a case of the embodiment in which publicly known mutation information is downloaded in accordance with an instruction from a user, the reference sequence management unit 112 may present to the user the date on which publicly known mutation information was downloaded at the immediately preceding time. Accordingly, it is possible to notify the user in advance whether or not the downloaded publicly known mutation information is new and appropriate.

Here, data which is stored in the gene panel information database 121 and which is referred to by the reference sequence management unit 112 when information regarding a gene panel has been inputted through the input unit 15 is described with reference to FIG. 5. FIG. 5 is diagram showing an example of a data structure of the gene panel information database 121.

In the gene panel information database 121, as shown in data 121A in FIG. 5, the name of each gene that can be an analysis target of a gene panel and a gene ID provided to the gene are stored in association with each other. In addition, in the gene panel information database 121, as shown in data 121B in FIG. 5, the name of each selectable gene panel, the gene panel ID provided to the gene panel, and gene Ms of analysis target genes of the gene panel are stored in association with one another.

When a gene panel name has been inputted by the user through the input unit 15, the reference sequence management unit 112 may refer to the gene panel information database 121 and extract the gene name, the gene panel ID, and related gene IDs which are associated with the inputted gene panel name.

When gene names have been inputted by the user through the input unit 15, the reference sequence management unit 112 may refer to the gene panel information database 121 and extract the gene IDs associated with the inputted gene names, and the gene panel ID of a gene panel associated with these gene IDs.

In the gene panel information database 121, as shown in data 121C in FIG. 5, the name of a gene panel regarding a disease and the analysis target gene names of the gene panel may be stored in association with each other.

When a disease name has been inputted by the user through the input unit 15, the reference sequence management unit 112 may refer to the gene panel information database 121 and extract related gene IDs and a gene panel ID, on the basis of the gene panel name or the gene names associated with the inputted disease name.

On the basis of the downloaded publicly known mutation information, the reference sequence management unit 112 generates a rearrangement sequence and adds/saves the generated rearrangement sequence in the reference sequence database 122. For example, by use of a partial sequence or a complete sequence of a wild type, and the chromosome number, the position, and mutation sequence a of a mutation indicated by publicly known mutation information, the reference sequence management unit 112 generates a rearrangement sequence that includes the mutation sequence a. Accordingly, the rearrangement sequence becomes a sequence in which a known polymorphism, mutation, methylation, or the like that has occurred in a partial sequence or a complete sequence of an exon or the like of a wild type has been reproduced.

Here, a data structure of the reference sequence database 122 is described with reference to FIG. 6. Data 122A shown in FIG. 6 is a diagram showing one example of a data structure of the reference sequence database 122 which stores rearrangement sequences generated by the reference sequence management unit 112. This example shows rearrangement sequences which have been generated by the reference sequence management unit 112 on the basis of known mutation information such that the rearrangement sequences include known mutations that have occurred in the gene having a gene name "EGFR". Each generated rearrangement sequence is, without being limited to this embodiment, stored in association with the gene name (or related gene ID) used in generation of the rearrangement sequence, the rearrangement sequence ID provided to the rearrangement sequence, the length of the rearrangement sequence, the length from the 5' end of the rearrangement sequence to the mutation sequence, and the like. Further, each rearrangement sequence may be stored in association with the mutation ID of the mutation included in the rearrangement sequence, the mutation sequence, the chromosome number, and the position of the mutation on the chromosome indicated by the chromosome number. For example, in the data 122A shown in FIG. 6, rearrangement sequence aa having a rearrangement sequence ID "aa" is a sequence generated by inserting mutation sequence a at a position that corresponds to the position "pa" on the chromosome of the chromosome number "CHa" in the complete sequence or a partial sequence of the wild type "EGFR" sequence. The entire length of the rearrangement sequence aa is 325 bases, and the length from the 5' end to the position where the mutation sequence a is inserted is na bases. As shown in the data 122A in FIG. 6, rearrangement sequences that include mutation sequences at different positions in the same gene, rearrangement sequences that include different mutations at the same position of the same gene, and the like are provided with individual rearrangement sequence IDs.

With reference back to FIG. 4, the reference sequence generation unit 115 reads out rearrangement sequence aa, rearrangement sequence bb, rearrangement sequence cc, . . . , and rearrangement sequence xx from the reference sequence database 122, and connects the rearrangement sequences into one piece according to a predetermined connection method, thereby generating a single reference sequence. In the reference sequence database 122, wild-type reference sequences are stored in addition to reference sequences and rearrangement sequences having incorporated therein mutation sequences.

Figure 7A:
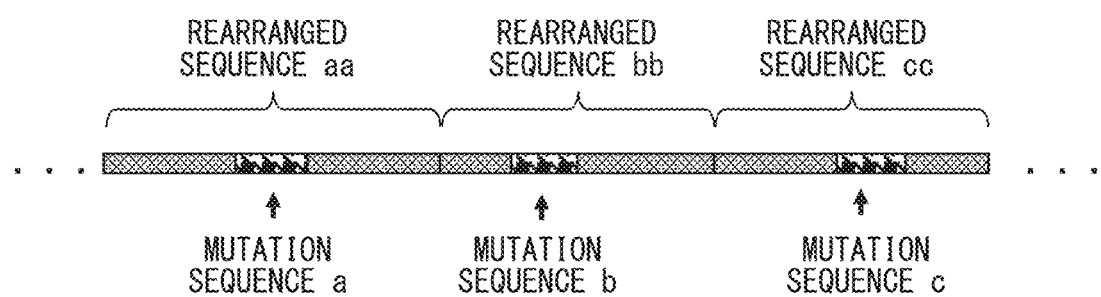
FIG. 7A is a conceptual diagram describing an example of a reference sequence generation method.
Figure 7B:
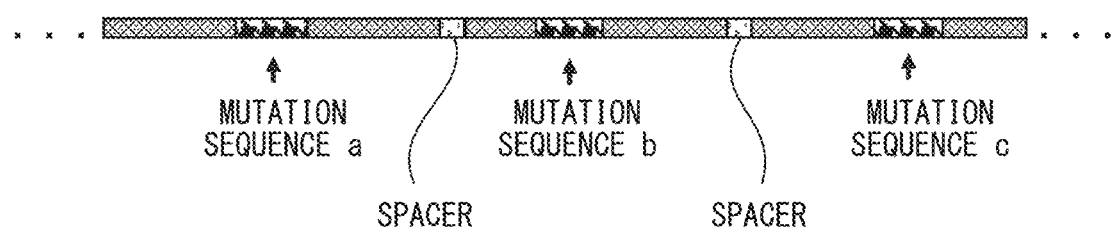
FIG. 7B is a conceptual diagram describing another example of the reference sequence generation method.

As shown in FIG. 7A, as the method by which the reference sequence generation unit 115 connects rearrangement sequences into one piece, rearrangement sequence aa (first rearrangement sequence), rearrangement sequence bb (second rearrangement sequence), and rearrangement sequence cc (third rearrangement sequence), and so on may be directly connected to one another without any base being inserted therebetween. Alternatively, as shown in FIG. 7B, a spacer sequence having a predetermined length may be inserted in the connection portions between rearrangement sequence aa, rearrangement sequence bb, rearrangement sequence cc, and so on. As the spacer sequence, a sequence composed of 10 consecutive guanines may be used, for example. The spacer sequence may be composed of a character string other than A, T, G, and C. For example, gene names such as "AKT1" and "EGFR"; characters included in Greek alphabets such as α and β; Roman numerals such as I, VI, and IX; and a predetermined number of digits such as "20170901" may be inserted. By inserting a spacer sequence also including a character string other than A, T, G, and C, it becomes possible to ignore the possibility that a read sequence is mapped onto a region that extends over two adjacent rearrangement sequences in the reference sequence, i.e., the connection portion that connects two rearrangement sequences. It should be noted that, in some cases, character "N" included in English alphabets is used, in the reference sequence, as a character that means a nucleotide that matches any of A, T, C, and G in the read sequence. Therefore, preferably, using "N" as a spacer sequence is avoided as much as possible.

The reference sequence generated by the reference sequence generation unit 115 is provided with a reference sequence ID such as "egfr-20170801" by the reference sequence management unit 112, and is saved in the reference sequence database 122.

Data 122B shown in FIG. 6 is a diagram showing one example of a data structure of the reference sequence database 122 which stores the reference sequences generated by the reference sequence generation unit 115. Each reference sequence is stored in association with a reference sequence ID and the generation date on which the reference sequence was generated by the reference sequence generation unit 115. The reference sequence ID may include information indicating the generation date on which the reference sequence was generated. For example, in the example of the data 122B shown in FIG. 6, the reference sequence generated on Sep. 1, 2017 for a gene having a gene name "BRAF" is provided with a reference sequence ID "braf-20170901". The reference sequence generated on Aug. 1, 2017 for a gene having a gene name "EGFR" is provided with a reference sequence ID "egfr-20170801". In this manner, if the reference sequence ID or the like of a reference sequence generated by connecting rearrangement sequences into one piece includes information indicating the generation date of the reference sequence, it is possible to easily notify the user when the reference sequence was generated. A preferable embodiment is, but not limited to, an embodiment in which the reference sequence generation unit 115 generates a reference sequence when, for example, the reference sequence management unit 112 has obtained publicly known mutation information from the mutation information database 3; or known mutation information in a mutation information database 3a has been updated.

The reference sequence stored in the reference sequence database 122 is referred to by the sequence determination unit 113 when the sequence determination unit 113 performs alignment of read sequences of nucleic acid fragments.

<Flow of Process of Generating and Updating Single Reference Sequence>

One example of the flow of a process of generating and updating a single reference sequence is described with reference to the flow chart shown in FIG. 8.

First, in step S1 shown in FIG. 8, the reference sequence management unit 112 specifies a gene as an analysis target. For example, the reference sequence management unit 112 may periodically specify all the genes as analysis targets of the sequence analysis apparatus 1, or may receive an input such as a gene panel name, gene names, and the like from the user through the input unit 15, for specifying genes as analysis targets.

When the specified gene is a gene that is analyzed for the first time by use of the sequence analysis apparatus 1 (YES in step S2), the reference sequence management unit 112 downloads, from the mutation information database 3, all pieces of publicly known mutation information of the gene, the mutation ID provided to each of the publicly known mutation information, the date on which information regarding each mutation was uploaded, and the like (step S3). However, not limited thereto, on the basis of information regarding each mutation downloaded from the external mutation information database 3, the user may create a specific file and the created file may be uploaded to a mutation information database 3a included in the test institution 110. It should be noted that "sequence information of known mutations" to be downloaded may not be all the pieces of publicly known mutation information uploaded in the mutation information database 3. For example, "sequence information of known mutations" may be limited to publicly known mutation information regarding mutations, among polymorphism, mutation, and methylation that occur in the specified gene, that are known to be related to diseases.

Specifically, through the communication unit 16, the reference sequence management unit 112 transmits the gene ID of the specified gene and a mutation information request to the mutation information database 3, and downloads desired publicly known mutation information designated by this request, from the mutation information database 3. A mutation information request may be periodically transmitted at a predetermined interval (for example, every day, once a week, or once a month), or may be transmitted every time the user uses the sequence analysis apparatus 1. Alternatively, the sequence analysis apparatus 1 may obtain a notification to the effect that information regarding a new mutation has been uploaded to the mutation information database 3. In this case, every time the notification is obtained, a mutation information request may be transmitted from the sequence analysis apparatus 1.

Next, the reference sequence management unit 112 generates a rearrangement sequence that corresponds to each of the publicly known mutation information downloaded in step S3, and saves the rearrangement sequences in the reference sequence database 122 (step S4).

The reference sequence generation unit 115 reads out generated rearrangement sequences from the reference sequence database 122, and connects the rearrangement sequences into one piece according to a predetermined connection method, to generate a reference sequence (step S5).

The reference sequence generated by the reference sequence generation unit 115 is provided with a reference sequence ID by the reference sequence management unit 112, and is saved in the reference sequence database 122 (step S6).

Meanwhile, when the specified gene is not a gene that is analyzed for the first time by use of the sequence analysis apparatus 1 (NO in step S2), the reference sequence management unit 112 determines, with respect to the gene, the presence or absence of information regarding any mutation that was uploaded to the mutation information database 3 after the date on which publicly known mutation information was downloaded at the immediately preceding time (step S7).

When there is information regarding a mutation that was uploaded after the date on which publicly known mutation information was downloaded at the immediately preceding time (YES in step S7), the reference sequence management unit 112 downloads the new publicly known mutation information, generates a rearrangement sequence by use of the publicly known mutation information and saves the generated rearrangement sequence (step S8).

The reference sequence generation unit 115 obtains the reference sequence stored in the reference sequence database 122 and the newly generated rearrangement sequence, and connects these into one piece according to a predetermined connection method, to generate a new reference sequence (step S9). That is, the reference sequence generation unit 115 reads out the reference sequence stored in the reference sequence database 122, and connects the rearrangement sequence newly generated by the reference sequence management unit 112 (for example, a rearrangement sequence including the mutation "C797S" shown in FIG. 4) to the rearrangement sequences already included in the reference sequence, thereby updating the reference sequence. In the example shown in FIG. 4, the reference sequence generation unit 115 connects a rearrangement sequence including the mutation "C797S" to the rearrangement sequence at the end of the reference sequence read out from the reference sequence database 122. However, not limited thereto, the reference sequence generation unit 115 may update the reference sequence by inserting the rearrangement sequence newly generated by the reference sequence management unit 112 into a connection portion of rearrangement sequences included in the reference sequence read out from the reference sequence database 122.

The reference sequence generated by the reference sequence generation unit 115 is stored in the reference sequence database 122 (step S10). As in data 122C shown in FIG. 6, for each reference sequence, a reference sequence ID provided to the reference sequence and connection information are stored in association with each other. The connection information is information that includes a rearrangement sequence ID of each rearrangement sequence used in generation of the reference sequence, information of the length of each rearrangement sequence, the connection order, and the like. As the connection information, the presence or absence of a spacer, and information regarding the length of the spacer may be included.

Meanwhile, when there is no information regarding any mutation that was uploaded after the date on which publicly known mutation information was downloaded at the immediately preceding time (NO in step S7), the reference sequence management unit 112 does not download publicly known mutation information. In addition, the reference sequence generation unit 115 does not update the reference sequence. Even when the reference sequence generation unit 115 does not update the reference sequence, the reference sequence management unit 112 preferably updates the reference sequence ID of the reference sequence stored in the reference sequence database 122. Accordingly, it is possible to notify the user that the reference sequence has been generated with the newest publicly known mutation information reflected. For example, irrespective of whether or not a new rearrangement sequence was connected to a rearrangement sequence included in the reference sequence having the reference sequence ID "egfr-20170801" on Sep. 1, 2017, a new reference sequence ID in which the portion of "20170801" of the reference sequence ID is updated with "20170901" may be provided.

Here, an example case where, for each gene, the reference sequence generation unit 115 generates one reference sequence by connecting rearrangement sequences has been described. However, the present disclosure is not limited thereto. For example, for each gene, a reference sequence may be created by connecting a wild-type reference sequence and rearrangement sequences into one piece, or a reference sequence may be created by connecting, into one piece, all the rearrangement sequences of the analysis target genes of the gene panel inputted by the user in step S1.

Alternatively, a reference sequence may be created by connecting, into one piece, all of the wild-type reference sequences and rearrangement sequences for the analysis target genes of the gene panel inputted by the user in step S1. For example, when a gene panel name "A panel" has been inputted by the user, the reference sequence generation unit 115 refers to the gene panel information database 121 and determines the gene ID or the gene name associated with the inputted gene panel name. One or a plurality of the gene names or gene IDs are determined. The reference sequence generation unit 115 may read out wild type sequences and rearrangement sequences associated with the determined gene names from the reference sequence database 122, and connect these into one piece. The reference sequence thus generated serves as the only one reference sequence that includes rearrangement sequences and that is to be used in alignment of read sequence information in the analysis using the gene panel. This reference sequence may be provided with, in addition to the generation date on which the reference sequence was generated, a reference sequence ID (for example, "A Panel 20170901") that includes information (for example, gene panel name) indicating the gene panel.

Next, in the test institution 110, pretreatment for allowing the sequencer 2 to analyze base sequences of a sample DNA is performed (step S52 in FIG. 3). The flow of the pretreatment is described with reference to the flow chart shown in FIG. 9A.

(Step S52: Pretreatment)

Figure 9A:
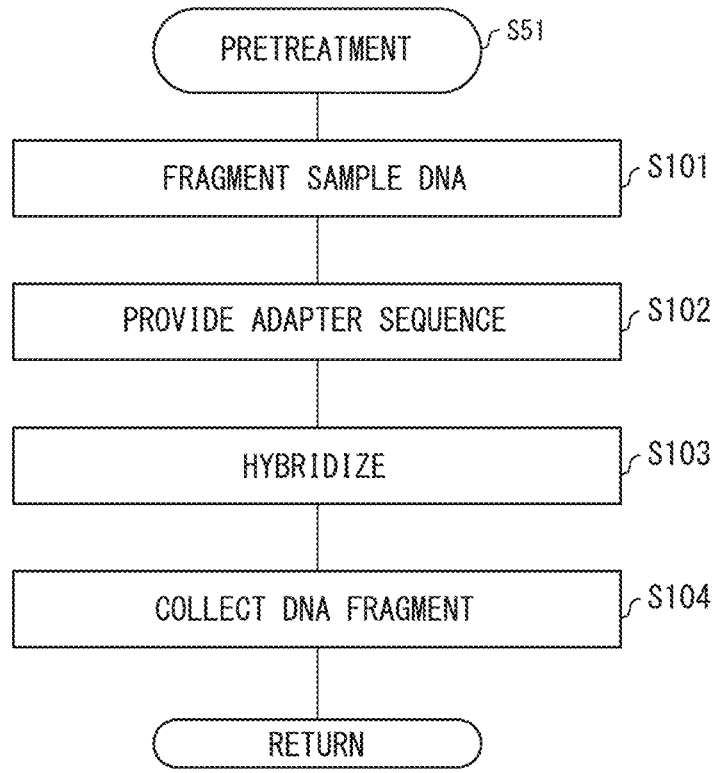
FIG. 9A is a flow chart describing one example of a procedure of pretreatment for analyzing base sequences of a sample DNA by a sequencer.

First, as shown in FIG. 10A, a sample (DNA) that includes DNA is fragmented so as to have a length at which the sequencer 2 reads a sequence (step S101 in FIG. 9A). Fragmentation of sample DNA can be performed by a known method such as ultrasonic treatment or treatment by a reagent that fragments nucleic acid, for example. However, since the fragmentation treatment in step S101 is not required in some cases, the fragmentation treatment is not indispensable. Each obtained DNA fragment (nucleic acid fragment) can have a length of several ten or several hundred bp, for example. In the following, an example case in which the gene as an analysis target is DNA is described, but the gene as an analysis target may be RNA.

Next, as shown in FIG. 10B, adapter sequences according to the type of the sequencer 2 and the sequencing protocol that are used are provided to both ends (3' end and 5' end) of each DNA fragment obtained in step S101 (step S102 in FIG. 9A). This step is indispensable when the sequencer 2 is a sequencer of Illumina, Inc. or an apparatus that employs a similar method to that of the sequencer of Illumina, Inc. However, when another type of sequencer 2 is used, this step can be omitted in some cases.

The adapter sequences are used in order to perform sequencing in the steps below. In one embodiment, the adapter sequences can be those to be hybridized to oligo DNA immobilized on a flow cell in a Bridge PCR method.

In one embodiment, as shown in the upper part of FIG. 10B, an adapter 1 sequence and an adapter 2 sequence may be directly added to both ends of the DNA fragment. For adding the adapter sequences to the DNA fragment, techniques known in this field can be used. For example, the DNA sequence may be blunted and ligated with adapter sequences.

In another embodiment, as shown in the lower part of FIG. 10B, index sequences may be inserted between both ends of the DNA fragment and the adapter sequences.

The index sequence is a sequence for distinguishing data of each sample. The index sequence is unique to each sample, each gene panel, and each company providing the gene panel. For example, a base sequence used as the index sequence has, but not limited to a given length; and a sequence pattern, such as 10 to 14 consecutive adenines, or 5 to 7 consecutive adenines followed by 5 to 7 consecutive guanines. With respect to the sequence of the DNA fragment having the index sequence added thereto, the index sequence can, on the basis of the sequence pattern and the length thereof, be used to identify information regarding which sample is the source of the sequence data; which gene panel was used; which company provided the gene panel used; and the like.

For example, the index sequence in an analysis using a gene panel A may have a sequence pattern of 14 consecutive adenines, and the index sequence in an analysis using a gene panel B may have a sequence pattern of 7 consecutive adenines followed by 7 consecutive guanines. Alternatively, the index sequence in an analysis using the gene panel A may have a sequence of 14 consecutive adenines (i.e., the length of the index sequence is 14), and the index sequence in an analysis using a gene panel C may have a sequence of 10 consecutive adenines (i.e., the length of the index sequence is 10).

For adding the index sequence and the adapter sequences to the DNA fragment, techniques known in this field can be used. For example, the DNA sequence may be blunted and ligated with the index sequence, and then, further ligated with the adapter sequences.

Figure 11:
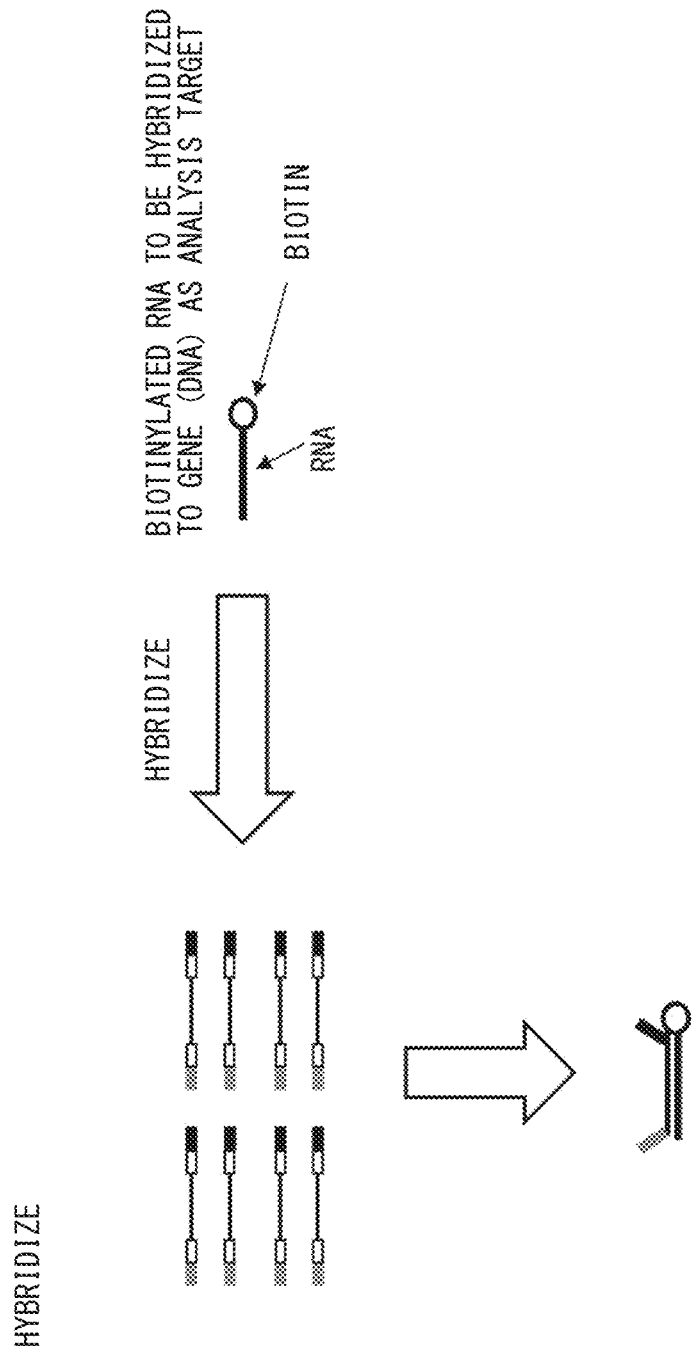
FIG. 11 is a diagram describing one example of a step of hybridization.

Next, as shown in FIG. 11, a biotinylated RNA bait library is hybridized to the DNA fragments provided with the adapter sequences (step S103 in FIG. 9). The biotinylated RNA bait library is composed of biotinylated RNAs (hereinafter, referred to as RNA bait) that are hybridized to genes as analysis targets. The RNA bait may have any length. However, in order to enhance specificity, for example, a long oligo RNA bait of about 120 bp may be used.

In the panel test using the sequencer 2 in the present embodiment, a large number of genes (for example, 100 or more) are analyzed. The reagent to be used in the panel test includes a set of RNA baits that respectively correspond to the large number of genes. When a different panel is used, the number and the types of analysis target genes are different, and thus, the set of RNA baits included in the reagent to be used in the panel test is also different.

As shown in FIG. 12, the DNA fragments as analysis targets are collected (step S104 in FIG. 9). Specifically, as shown in the upper part of FIG. 12, the DNA fragments hybridized with the biotinylated RNA bait library are mixed with streptavidin magnetic beads which are each composed of streptavidin and a magnetic bead bound to each other. Accordingly, as shown in the middle part of FIG. 12, the streptavidin part of the streptavidin magnetic bead and the biotin part of the RNA bait are bound to each other. Then, as shown in the lower part of FIG. 12, the streptavidin magnetic beads are collected by a magnet, and fragments that are not hybridized with the RNA baits (i.e., DNA fragments that are not analysis targets) are removed by washing. Accordingly, the DNA fragments hybridized with the RNA baits, i.e., the DNA fragments as analysis targets, can be selected and concentrated. The sequencer 2 reads the nucleic acid sequence of the DNA fragments selected by use of the plurality of RNA baits, thereby obtaining a plurality of read sequences.

Figure 13:
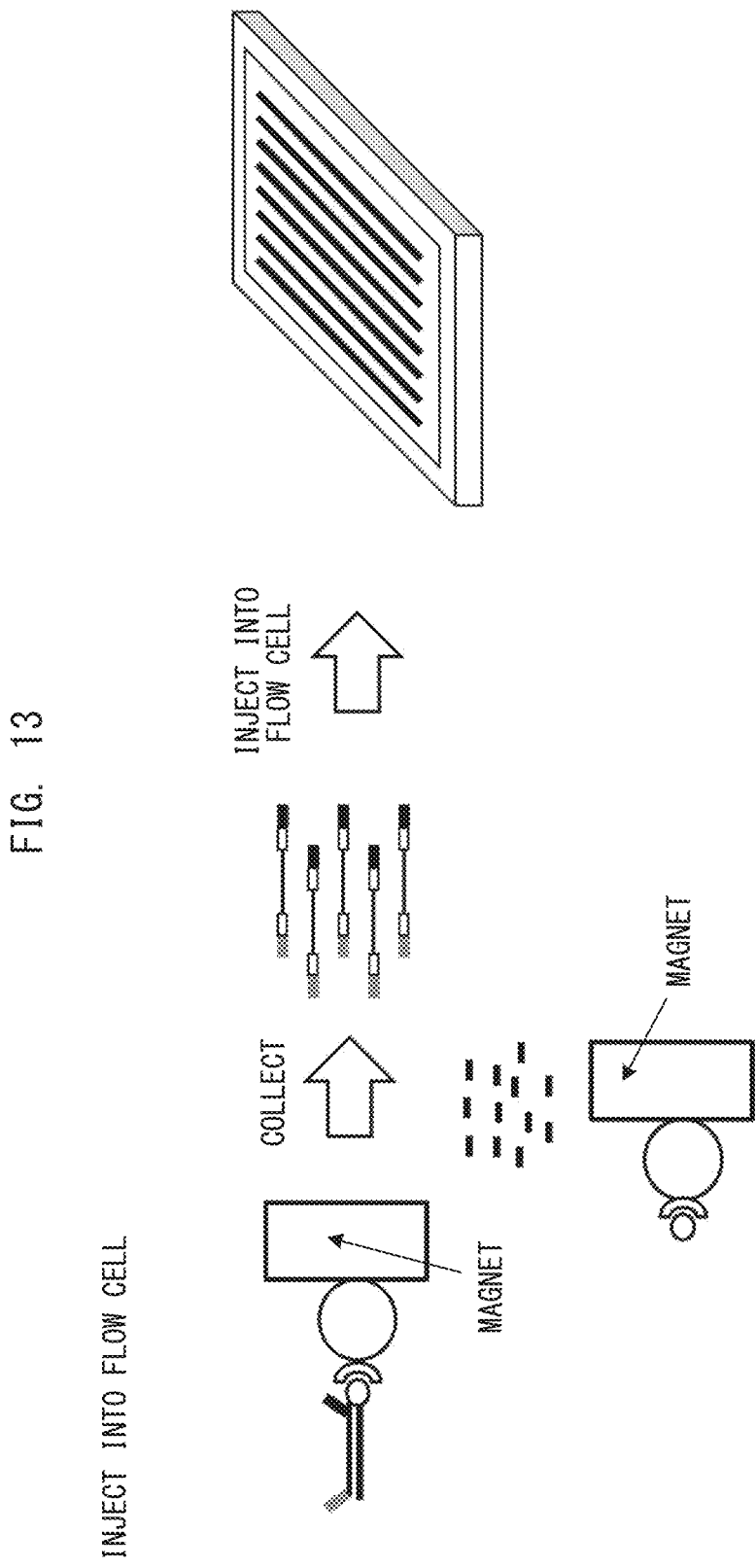
FIG. 13 is a diagram describing one example of a step of applying DNA fragments on a flow cell.

Further, as shown in the left section to the center section of FIG. 13, the streptavidin magnetic beads and the RNA baits are detached from the concentrated DNA fragments, and the resultant DNA fragments are amplified by PCR, whereby the pretreatment is completed.

Next, in the test institution 110, sequencing for reading base sequences of the sample DNA is performed (step S53 in FIG. 3). The flow of sequencing is described with reference to the flow chart shown in FIG. 9B.

The type of the sequencer 2 that can be used in the present embodiment is not limited in particular, and any sequencer that can analyze a plurality of analysis targets in one run can be suitably used. Examples of such a sequencer include: MySeq9 (registered trademark), HiSeq (registered trademark), and NextSeq (registered trademark) of Illumina, Inc. (San Diego, CA); Ion Proton (registered trademark) and Ion PGM (registered trademark) of Thermo Fisher (Waltham, MA); and GS FLX+ (registered trademark) and GS Junior (registered trademark) of Roche (Basel, Switzerland). In the following, one example is described in which a sequencer of Illumina, Inc., or an apparatus that employs a similar method to that of the sequencer of Illumina, Inc. is used. Through a combination of a Bridge PCR method and a Sequencing-by-synthesis technique, the sequencer of Illumina, Inc. can perform sequencing, with analysis target DNA amplified and synthesized to a huge number on a flow cell.

(Step S53: Sequencing)

Figure 9B:
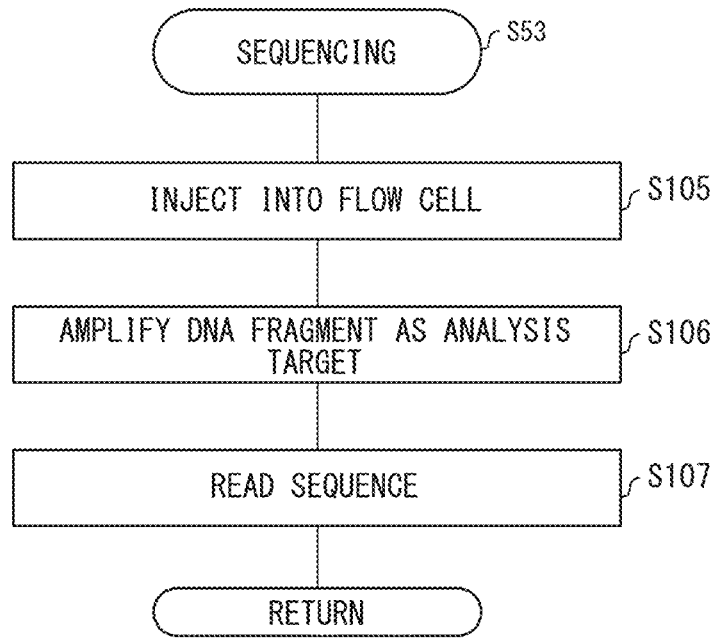
FIG. 9B is a flow chart describing one example of a procedure of sequencing.

First, as shown in the right section of FIG. 13, the amplified DNA fragments are applied on the flow cell (step S105 in FIG. 9B). Next, as shown in FIG. 14, the DNA fragments as analysis targets are amplified on the flow cell through Bridge PCR (step S106 in FIG. 9B).

That is, each DNA fragment as an analysis target (Template DNA in FIG. 14) is in a state in which both ends of the DNA fragment have two different types of adapter sequences (adapter 1 sequence and adapter 2 sequence) added thereto ("1" in FIG. 14) through the above-described pretreatment. This DNA fragment is separated into single strands, and the adapter 1 sequence at the 5' end side is immobilized on the flow cell ("2" in FIG. 14). On the flow cell, the adapter 2 sequence at the 3' end side is immobilized in advance. The adapter 2 sequence at the 3' end side of the DNA fragment is bound to the adapter 2 sequence at the 3' end side on the flow cell to produce a bridge-like state (bridge) ("3" in FIG. 14). In this state, DNA elongation is caused by a DNA polymerase ("4" in FIG. 14) and denaturation is caused, whereby two single-stranded DNA fragments are obtained ("5" in FIG. 14). Through repetition of the bridge formation, the DNA elongation, and the denaturation in this order, a large number of single-stranded DNA fragments are locally amplified and immobilized, whereby clusters can be formed ("6" to "9" in FIG. 14).

Figure 14:
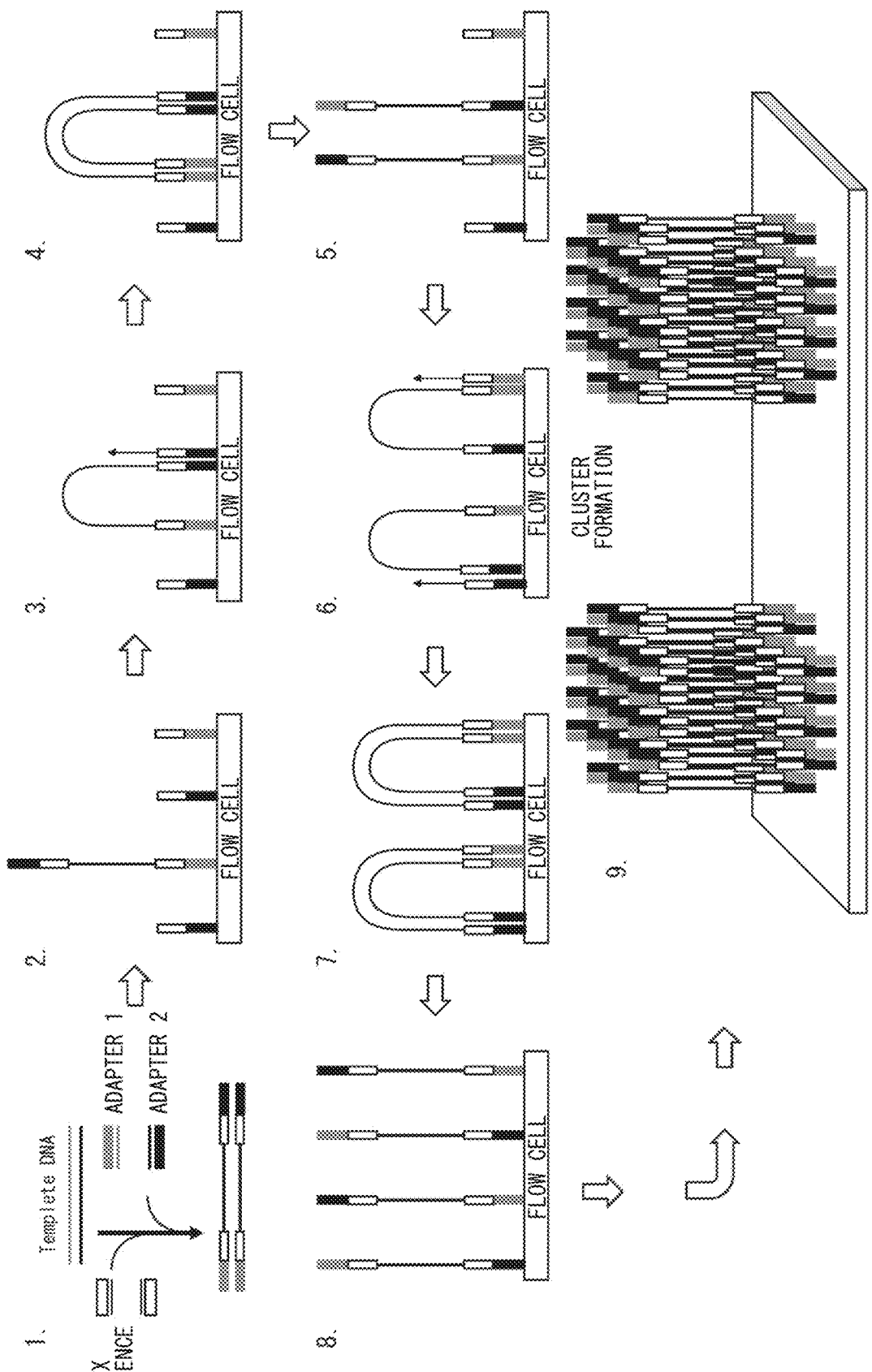
FIG. 14 is a diagram describing one example of a step of amplifying DNA fragments as analysis targets.

Then, as shown in FIG. 14, with each single-stranded DNA forming a cluster used as a template, the sequence is read through Sequencing-by-synthesis (step S107 in FIG. 9B).

Figure 15:
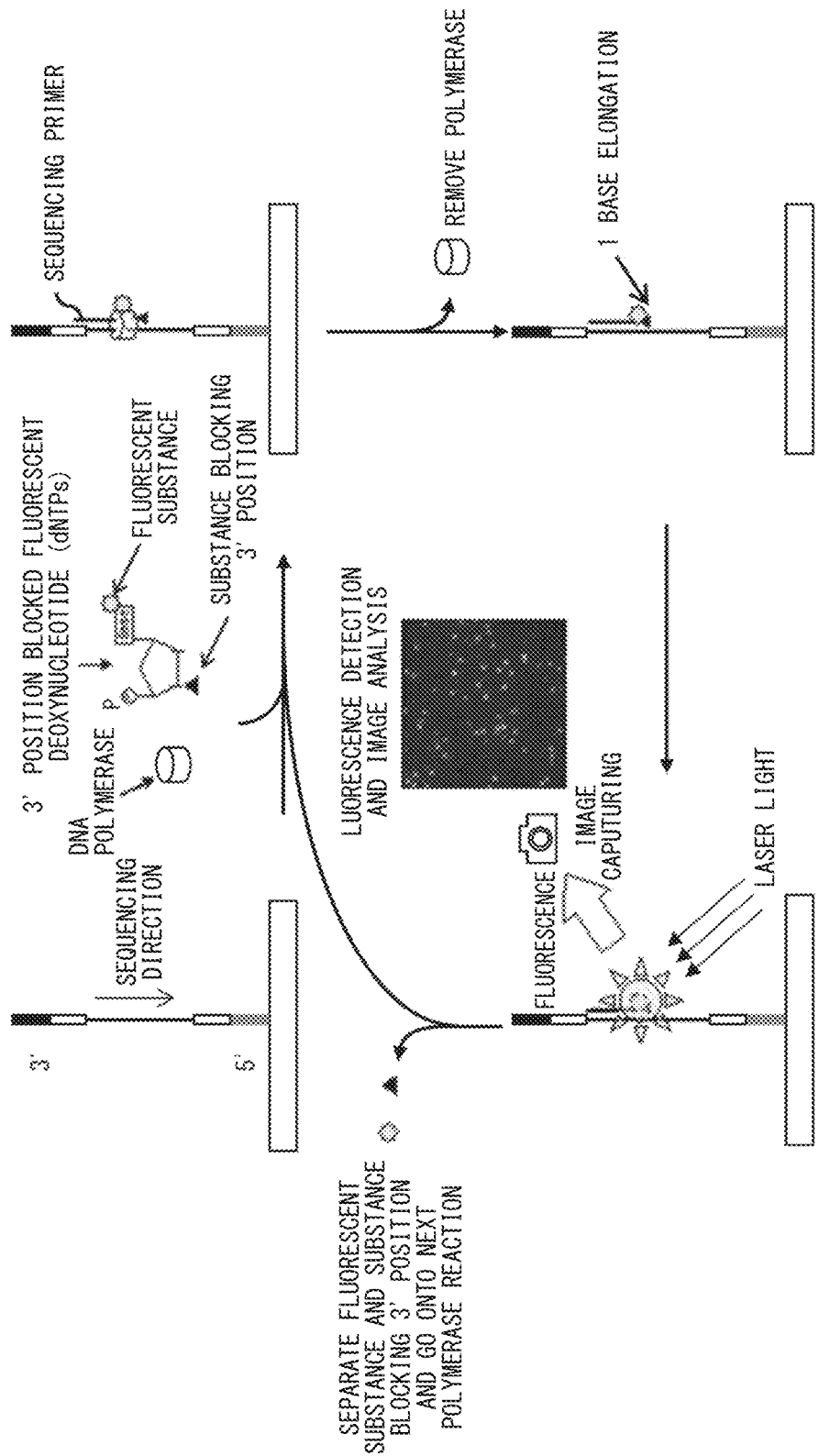
FIG. 15 is a diagram describing one example of a sequencing step.

First, to the oligo DNA immobilized on the flow cell (for example, the single-stranded DNA shown in the left section in the upper part of FIG. 15), a DNA polymerase, and dNTP that is fluorescently labeled and of which 3' end side is blocked are added (the center section in the upper part of FIG. 15), and further, a sequencing primer is added (the right section in the upper part of FIG. 15). The sequencing primer may be any sequencing primer that is designed to be hybridized to a part of the adapter sequence, for example. In other words, it is sufficient that the sequencing primer is designed to amplify a sample DNA-derived DNA fragment. In a case where an index sequence has been added, it is sufficient that the sequencing primer is designed to further amplify the index sequence.

After addition of the sequencing primer, one base elongation of the 3' end-blocked fluorescently-labeled dNTP is caused by the DNA polymerase. Since the dNTP of which 3' end side is blocked is used, the polymerase reaction stops when one base has been elongated. Then, the DNA polymerase is removed (the right section in the middle part of FIG. 15). Then, laser light is applied to the single-stranded DNA elongated by one base (the right section in the lower part of FIG. 15) to excite the fluorescent substance bound to the base, and a photograph of the light generated at that time is taken and recorded (the left section in the lower part of FIG. 15). In order to determine four types of bases, the photographs are taken by a fluorescence microscope for the respective fluorescent colors that correspond to A, C, G, and T, with the wavelength filter changed. After all of the photographs have been taken, the bases are determined from the photograph data. Then, the fluorescent substance and the protecting group blocking the 3' end side are removed, and the reaction goes onto the next polymerase reaction. With this flow assumed as one cycle, the second cycle, the third cycle, and so on are performed, whereby sequencing of the entire length can be performed.

According to the technique described above, the length of the chain that can be analyzed reaches 150 bases×2, and analysis in a unit much smaller than the unit of a picoliter plate can be performed. Thus, due to the high density, huge sequence information of 40 to 200 Gb can be obtained in one analysis.

The gene panel used when read sequences are read by the sequencer 2 denotes an analysis kit for analyzing a plurality of analysis targets in one run as described above, and, in one embodiment, can be an analysis kit for analyzing a plurality of gene sequences regarding a specific disease.

When used herein, the term "kit" is intended to mean a package that includes containers each containing a specific material. Examples of the containers include bottles, plates, tubes, and dishes. Preferably, the kit includes an instruction insert for using each material. When used in a context regarding a kit herein, "include" is intended to mean a state where the thing that is included is contained in any of the individual containers forming the kit. The kit can be a package in which a plurality of different compositions are packed. Here, the forms of the compositions can be the forms as described above, and in the case of a solution form, the solution may be contained in a container. The kit may include a substance A and a substance B that are mixed in one container or that are in separate containers. The "instruction insert" indicates information regarding each component in the kit, such as information regarding the procedure in a case where the kit is applied to a therapy and/or a diagnosis. The "instruction insert" may be written or printed on paper or any other medium, or may be in the form of an electronic medium such as a magnetic tape, a computer readable disk or tape, or a CD-ROM. The kit can include a container which contains a diluent, a solvent, a washing liquid, or another reagent. Further, the kit may also include an apparatus that is necessary for the kit to be applied to a therapy and/or a diagnosis.

In one embodiment, the gene panel may be provided with one or more of the reagents such as: the reagent that fragments nucleic acid; the ligation reagent; the washing liquid; the PCR reagent (dNTP, DNA polymerase, etc.) such as dNTP, DNA polymerase; and the magnetic bead, which are described above. The gene panel may be provided with one or more of: oligonucleotides for adding the adapter sequences to the fragmented DNA; oligonucleotides for adding the index sequence to the fragmented DNA; the RNA bait library; the sequencing primer to be used in sequencing; and the like. Further, the gene panel may include: a flow cell in which predetermined oligo DNA is immobilized on at least a part of the surface thereof; a reagent for immobilizing the oligo DNA to at least a part of the surface of the flow cell; and the like.

In particular, the index sequence provided to each gene panel can be a sequence that is unique to the gene panel and that identifies the gene panel. The RNA bait library provided to each gene panel can be a library that is unique to the gene panel and that includes RNA baits that correspond to test genes of the gene panel.

Next, in the test institution 110, an analysis process of the read sequences that have been read is performed (step S54 in FIG. 3).

(Step S54: Analysis of Read Sequence)

The analysis process of read sequences is performed by the read sequence information obtaining unit 111, the sequence determination unit 113, and the mutation identification unit 114 of the controller 11. One example of the flow of the analysis is described with reference to the flow chart of FIG. 16.

Figure 16:
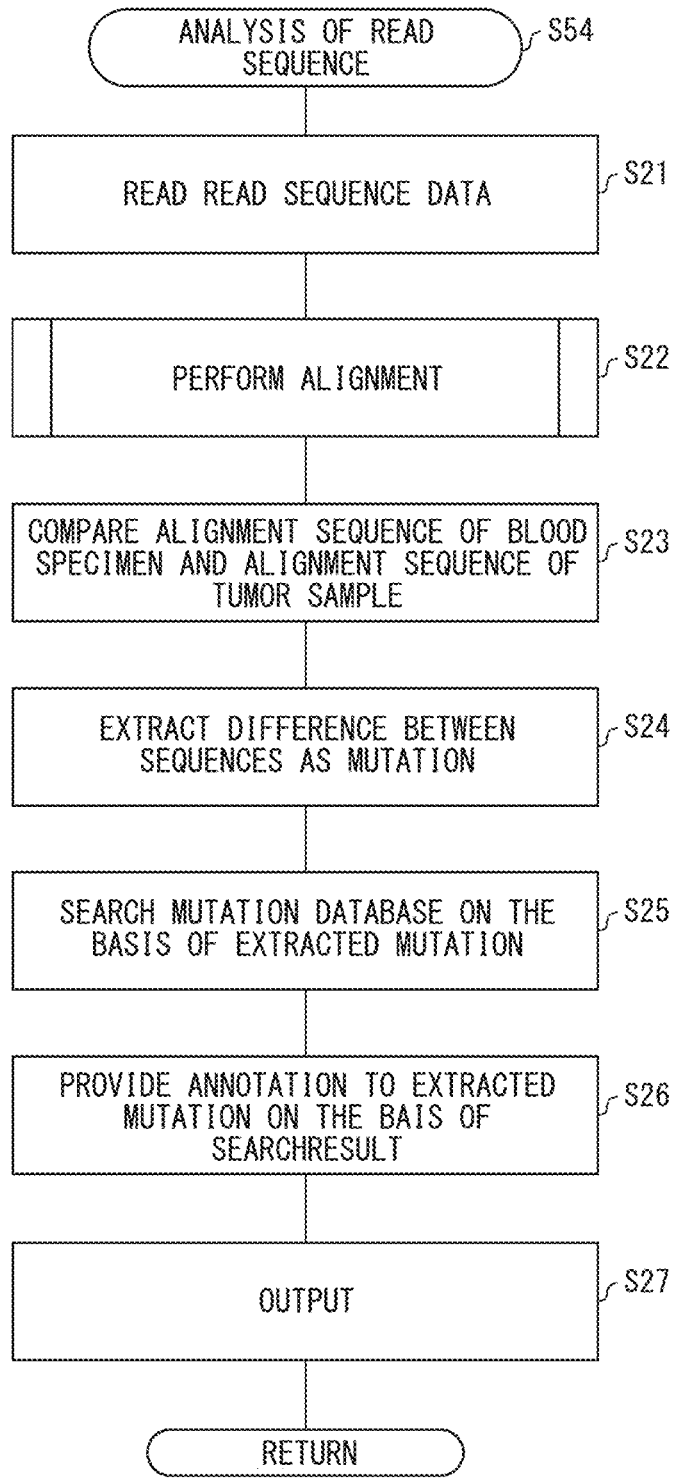
FIG. 16 is a flow chart describing one example of the flow of read sequence analysis performed by the sequence analysis apparatus.

First, the read sequence information obtaining unit 111 reads read sequence information provided from the sequencer 2 (step S21 in FIG. 16).

The read sequence information is data that indicates the base sequence read by the sequencer 2. The sequencer 2 performs sequencing on a large number of nucleic acid fragments; reads the sequence information thereof; and provides the sequence information, as read sequence information, to the sequence analysis apparatus 1. The read sequence information that has been read may be the sequences, of genes as analysis targets, that have been read in the panel test.

In one embodiment, the read sequence information may include the sequence that has been read and a quality score of each base in the sequence. Both of read sequence information obtained by subjecting to the sequencer 2 an FFPE sample collected from a lesion site of a subject, and read sequence information obtained by subjecting to the sequencer 2 a blood sample of the subject are inputted to the sequence analysis apparatus 1. A "subject" herein denotes a human subject or a subject that is not human such as a mammal, an invertebrate, a vertebrate, a fungus, a yeast, a bacterium, a virus, or a plant. The "FFPE sample" denotes a formalin-fixed paraffin-embedded sample.

FIG. 17 is a diagram showing one example of a file format of read sequence information. In the example shown in FIG. 17, the read sequence information includes a sequence name, a sequence, and a quality score. The sequence name indicates the sequence ID or the like provided to the read sequence information outputted by the sequencer 2. The sequence indicates the base sequence read by the sequencer 2. The quality score indicates the probability of incorrect base assignment performed by the sequencer 2. Any base sequencing quality score (Q) is represented by the following formula.

$$Q = -10 \log_{10} E$$

In this formula, E represents an estimated value of the probability of incorrect base assignment. A greater Q value means that the error probability is low. When the Q value decreases, the part that cannot be used in the read increases. In addition, false-positive mutation assignment also increases, which could result in a lower accuracy of the result. "False-positive" means that, although the read sequence does not have any true mutation as a target of the determination, the read sequence is determined as having a mutation. "Positive" means that the read sequence has a true mutation as a target of the determination. "Negative" means that the read sequence does not have any mutation as a target of the determination.

Next, on the basis of the read sequence information read by the read sequence information obtaining unit 111, the sequence determination unit 113 performs alignment of the read sequence of each nucleic acid fragment included in the read sequence information (step S22 in FIG. 16). Here, an example case is described in which the sequence is determined from read sequence information obtained by subjecting an FFPE sample to the sequencer 2, but the present disclosure is not limit thereto.

Figure 18:
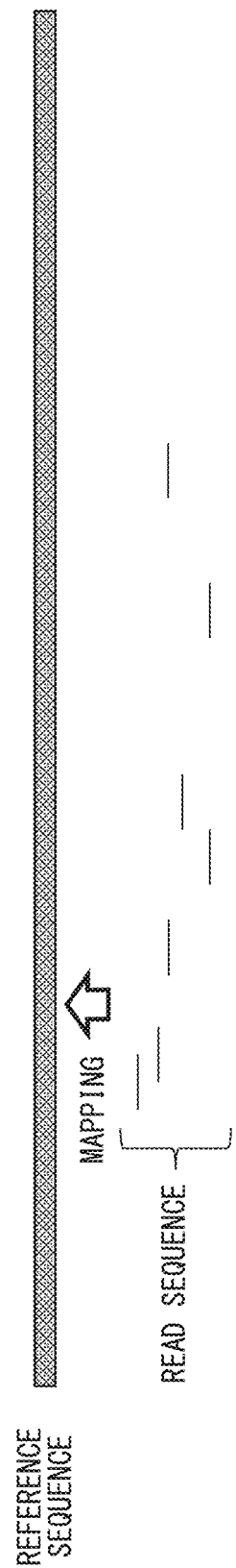
FIG. 18 is a diagram describing alignment performed by a sequence determination unit.

FIG. 18 is a diagram describing alignment performed by the sequence determination unit 113. The sequence determination unit 113 refers to a wild-type reference sequence and a single reference sequence stored in the reference sequence database 122, and maps the read sequence of each nucleic acid fragment to the reference sequence, thereby performing alignment.

The sequence determination unit 113 performs alignment with respect to both of read sequence information obtained by subjecting to the sequencer 2 an FFPE sample collected from a lesion site of a subject, and read sequence information obtained by subjecting a blood sample of the subject to the sequencer 2.

One example of a format of a file for outputting a result of alignment performed by the sequence determination unit 113 is described. The format of the alignment result is not limited in particular as long as the format can specify the read sequence, the reference sequence, and the mapping position. The format may include reference sequence information, read sequence name, position information, map quality, and sequence.

"Reference sequence information" indicates the reference sequence name, the reference sequence ID, the sequence length of the reference sequence, and the like. "Read sequence name" is the name, the read sequence ID, and the like of each read sequence for which the alignment was performed. "Position information" indicates the position on the reference sequence at which the leftmost base (the base at the 5' end) of the read sequence was mapped. "Map quality" is information regarding the mapping quality that corresponds to the read sequence, "Sequence" indicates the base sequence that corresponds to each read sequence.

Figure 19:
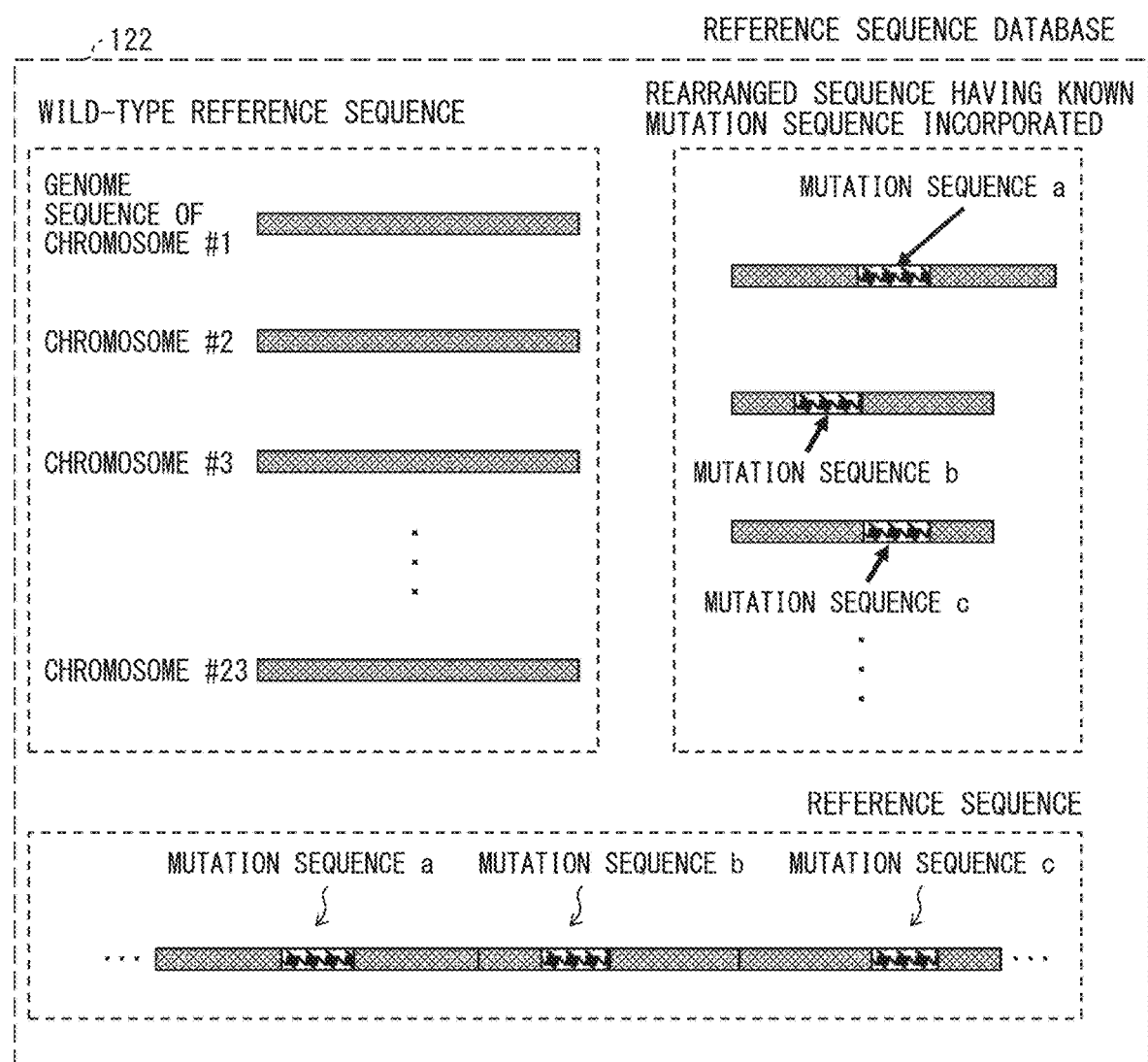
FIG. 19 is a diagram showing a structure example of a reference sequence database.

FIG. 19 is a diagram showing a structure example of the reference sequence database 122. As shown in FIG. 19, the reference sequence database 122 stores wild-type reference sequences (for example, genome sequences of chromosomes #1 to #23) indicating wild type sequences; rearrangement sequences each of which is a wild type sequence having a known mutation sequence incorporated therein; and a reference sequence obtained by connecting two or more rearrangement sequences into one piece.

FIG. 19 shows a single reference sequence obtained by connecting in order rearrangement sequence aa, rearrangement sequence bb, rearrangement sequence cc, and the like respectively including mutation sequence a, mutation sequence b, and mutation sequence c which have occurred in a certain exon sequence. However, the present disclosure is not limited thereto. For example, the connecting order is not limited thereto. Alternatively, the aforementioned spacer sequence may be inserted in a connection portion of rearrangement sequences. For example, rearrangement sequence cc may be connected immediately after rearrangement sequence aa, or rearrangement sequence cc may be connected immediately after rearrangement sequence bb.

FIG. 20 is a diagram showing an example of known mutations that are incorporated into rearrangement sequences and reference sequences included in the reference sequence database 122. The known mutations are mutations that are registered in the external mutation information database 3 such as COSMIC or ClinVar, for example, and of which chromosome position, gene name, and mutation are specified as shown in FIG. 20. In the example shown in FIG. 20, mutations of amino acid are specified. However, mutations of nucleic acid may be specified. The types of mutations are not limited in particular, and may be various mutations such as substitution, InDel, methylation, and a mutation in which a sequence of a part of another chromosome or a reverse complement sequence is bound.

Figure 21:
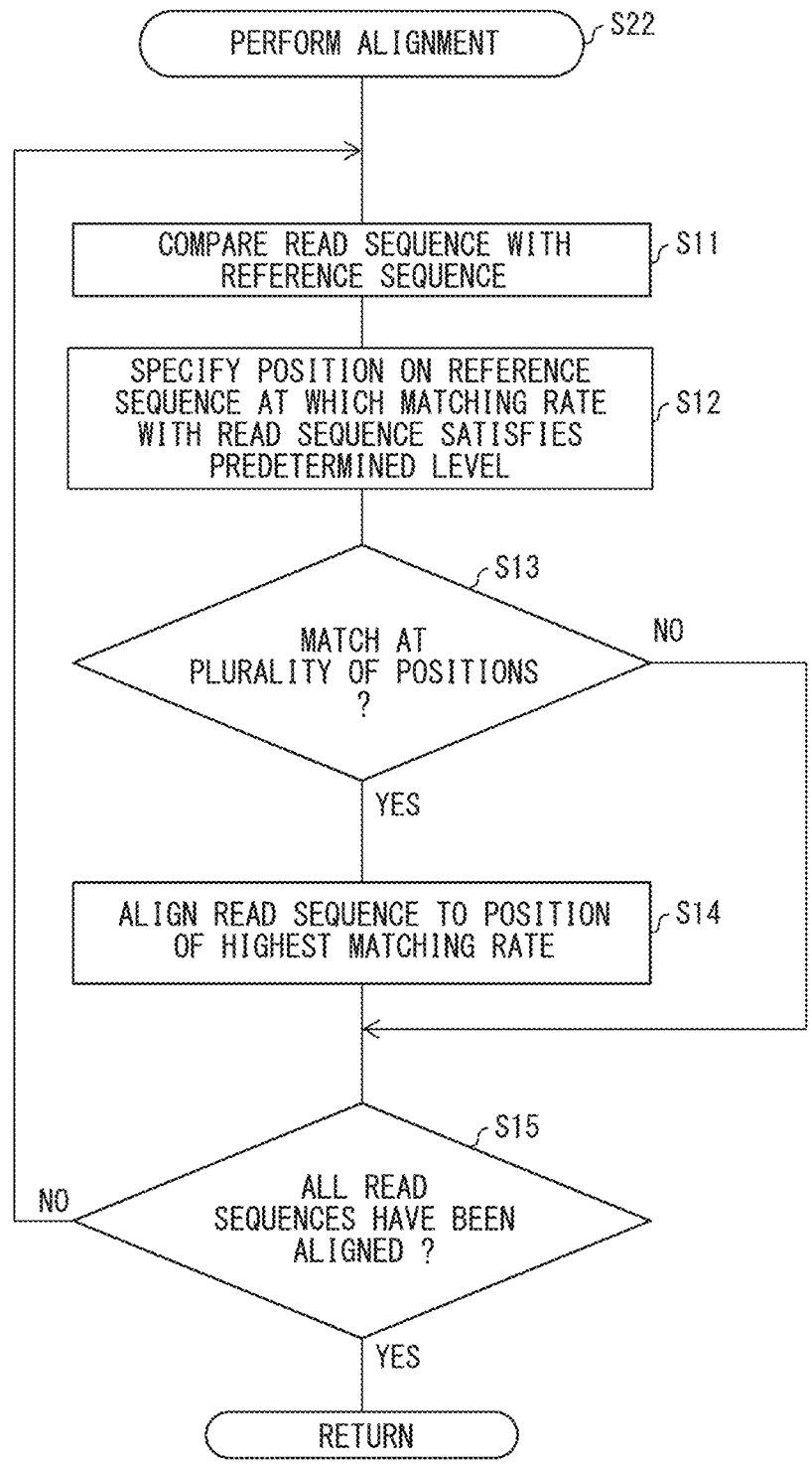
FIG. 21 is a flow chart describing one example showing details of a step of alignment.

FIG. 21 is a flow chart describing one example showing details of the steps of alignment performed in step S22 shown in FIG. 16.

Figure 22A:
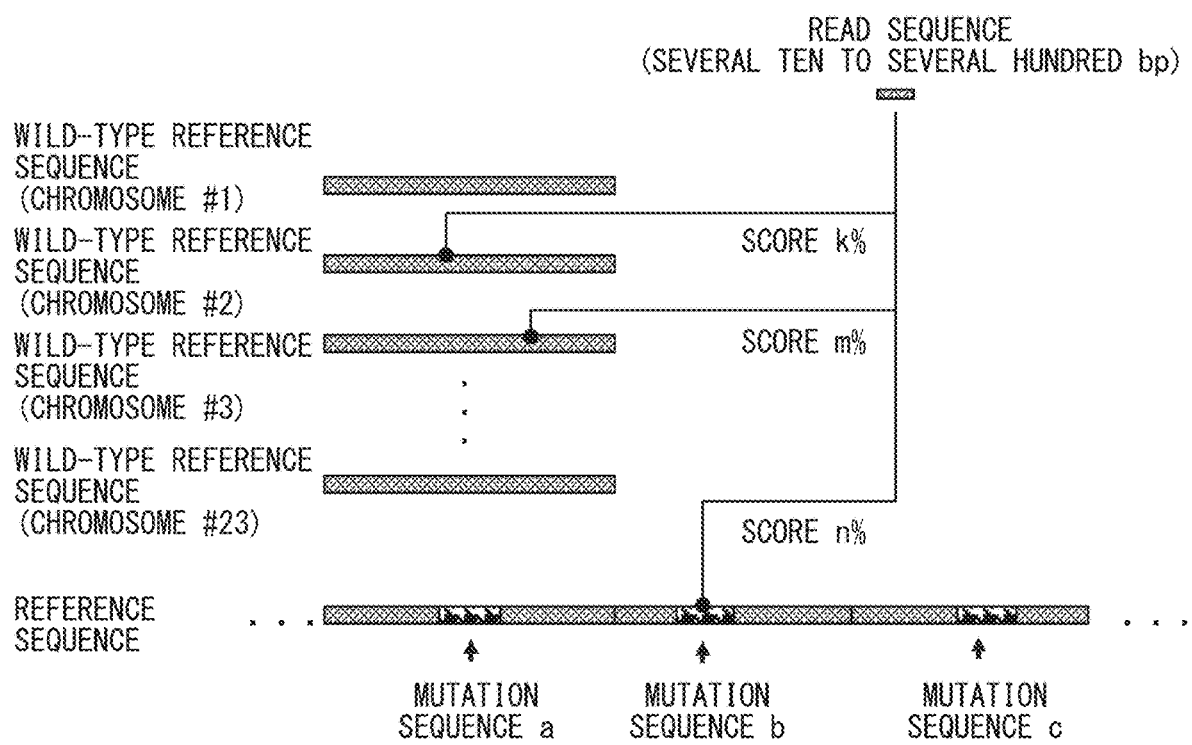
FIG. 22A is a diagram describing the outline of alignment performed by use of a reference sequence.
Figure 22B:
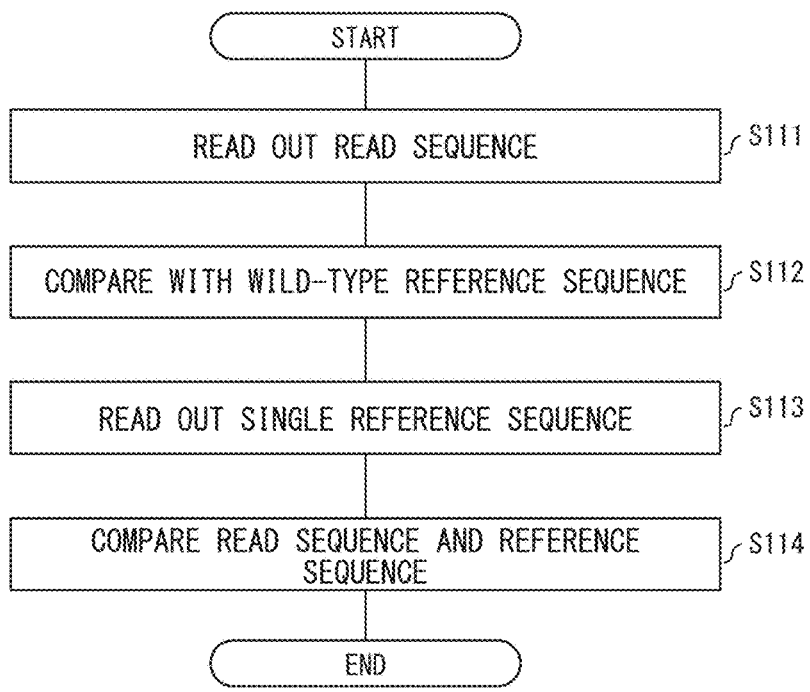
FIG. 22B is a flow chart showing one example of a process of mapping a read sequence by comparing the read sequence and a single reference sequence.

In step S11 shown in FIG. 21, the sequence determination unit 113 selects a read sequence for which alignment has not been performed from among the read sequences of the nucleic acid fragments included in the read sequence information obtained by the read sequence information obtaining unit 111, and compares the selected read sequence with the reference sequences (wild-type reference sequence and single reference sequence) obtained from the reference sequence database 122. FIG. 22B is a flow chart showing one example of the process of mapping a read sequence by comparing the read sequence with a single reference sequence. As shown in FIG. 22B, the sequence determination unit 113 reads out a read sequence (step S111), reads out a wild-type reference sequence from the reference sequence database 122, and compares the read sequence with the wild-type reference sequence (step S112). Next, the sequence determination unit 113 reads out a single reference sequence from the reference sequence database 122 (step S113), and compares the read sequence with the reference sequence (step S114). The order of the comparison between the read sequence and the wild-type reference sequence and the comparison between the read sequence and the reference sequence may be reversed. Then, in step S12, the sequence determination unit 113 specifies a position on the reference sequence at which the matching rate with the read sequence satisfies a predetermined level. Here, the matching rate is a value that indicates how much the obtained read sequence information and the reference sequence match each other. Examples of the matching rate include the number, proportion, or the like of bases that match each other.

In one embodiment, the sequence determination unit 113 calculates a score that indicates the matching rate between the read sequence and the reference sequence. The score indicating the matching rate can be a percentage identity between the two sequences, for example. As shown in FIG. 22A, the sequence determination unit 113 calculates the percentage, by identifying the positions at which bases of the read sequence and bases of the wild-type reference sequence and the single reference sequence are identical to each other, obtaining the number of positions at which the bases match each other, and dividing the number of positions at which the bases match each other by the number of bases of the read sequence compared with the reference sequence. The percentage calculated in this manner is the score indicating the matching rate.

FIG. 23A is a diagram showing one example of the score calculation. In one embodiment, at the positions shown in FIG. 23A, the score of the matching rate between read sequence R1 and the reference sequence is 100% because 13 bases among the 13 bases of the read sequence match; and the score of the matching rate between read sequence R2 and the reference sequence is 92.3% because 12 bases among the 13 bases of the read sequence match.

In the calculation of the score indicating the matching rate between a read sequence and a reference sequence, the sequence determination unit 113 may calculate such that, when the read sequence includes a predetermined mutation (for example, InDel) with respect to the reference sequence, a score lower than that in the normal calculation is obtained.

In one embodiment, with respect to the read sequence that includes at least one of insertion and deletion with respect to the reference sequence, the sequence determination unit 113 may correct the score by multiplying the score calculated in the normal calculation as described above by a weighting factor according to the number of bases that correspond to the InDel, for example. The weighting factor W may be calculated as W={1−(1/100)×(the number of bases that correspond to InDel)}, for example.

FIG. 23B is a diagram showing another example of the score calculation. In one embodiment, at the positions shown in FIG. 23B, in the normal calculation, the score of the matching rate between read sequence R3 and the reference sequence is 88% because 15 bases among the 17 bases of the read sequence (the symbol * indicating a deletion is calculated as one base) match. The corrected score is 86%=88%×0.98. In the normal calculation, the score of the matching rate between read sequence R4 and the reference sequence is 81% because 17 bases among the 21 bases of the read sequence match. The corrected score is 77.8%=81%× 0.96.

Figure 23C:
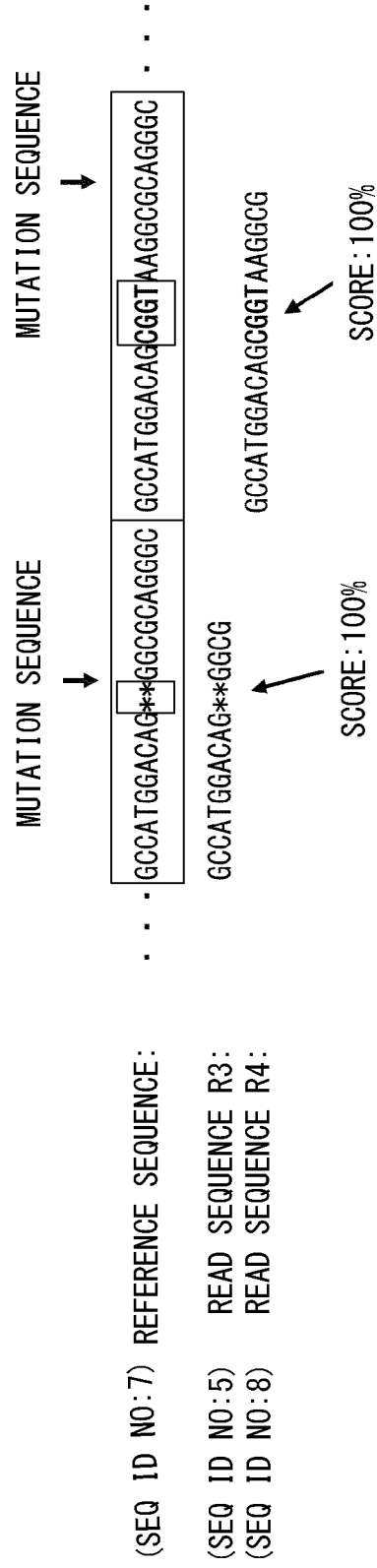
FIG. 23C is a diagram showing one example of score calculation performed by use of a reference sequence.

At the positions on the reference sequence shown in FIG. 23C, the score of the matching rate between read sequence R3 and the reference sequence is 100%, and the score of the matching rate between read sequence R4 and the reference sequence is also 100%. Thus, if the reference sequence is referred to, the score of the matching rate between the read sequence and the reference sequence is increased. Therefore, the possibility of mapping the read sequence to an incorrect position can be reduced, and the accuracy of the alignment can be improved.

By calculating the score of the matching rate while changing the mapping position of the read sequence with respect to each reference sequence, the sequence determination unit 113 specifies the position on the reference sequence at which the matching rate with the read sequence satisfies a predetermined level. At this time, an algorithm known in the field, such as FASTA or BLAST, may be used.

With reference back to FIG. 21, next, when the matching rate with the read sequence satisfies the predetermined level at a single position on the reference sequence (NO in step S13), the sequence determination unit 113 aligns the read sequence to the position. When the matching rate with the read sequence satisfies the predetermined level at a plurality of positions on the reference sequence (YES in step S13), the sequence determination unit 113 aligns the read sequence to the position at which the matching rate is highest (step S14).

When all of the read sequences included in the read sequence information obtained by the read sequence information obtaining unit 111 have not been aligned (NO in step S15), the sequence determination unit 113 returns to step S21. When all of the read sequences included in the read sequence information have been aligned (YES in step S15), the sequence determination unit 113 returns to the process in the flow chart shown in FIG. 16.

Next, the mutation identification unit 114 of the controller 11 compares an alignment sequence with which the read sequence obtained by subjecting the sample collected from a lesion site of the subject has been aligned, with an alignment sequence with which the read sequence obtained by subjecting the blood sample of the subject has been aligned (step S23 in FIG. 16). Then, the mutation identification unit 114 extracts the difference between the alignment sequences as a mutation (step S24 in FIG. 16). For example, if, at the same position of the same analysis target gene, the alignment sequence derived from the blood specimen is ATCGA and the alignment sequence derived from a tumor tissue is ATCCA, the mutation identification unit 114 extracts the difference of G and C as a mutation. In a case where the sample is not an FFPE sample but a blood sample, there is a possibility that cell free DNA is included in the blood sample, and thus, the process is advanced to step S24 without performing the process of step S23.

In one embodiment, the mutation identification unit 114 generates a result file on the basis of the extracted mutation. FIG. 24 is a diagram showing one example of a format of a result file generated by the mutation identification unit 114. The format is based on the Variant Call Format (VCF), for example. As shown in FIG. 24, in the result file, position information, reference base, and mutation base are described for each extracted mutation. The position information indicates the position on the reference genome, and includes the chromosome number and the position on the chromosome, for example. The reference base indicates the reference base (A, T, C, G, or the like) at the position indicated by the position information. The mutation base indicates the base of the reference base after the mutation. The reference base is the base on the alignment sequence derived from the blood specimen, and the mutation base is the base on the alignment sequence derived from the tumor tissue.

In FIG. 24, the mutation in which the reference base is C and the mutation base is G is an example of substitution mutation, the mutation in which the reference base is C and the mutation base is CTAG is an example of insertion mutation, and the mutation in which the reference base is TCG and the mutation base is T is an example of deletion mutation. The mutation in which the mutation base is G]17:198982],]13:123456]T, C[2:321682[, or [17:198983[A is an example of mutation in which a sequence of a part of another chromosome or a reverse complement sequence is bound.

With reference back to FIG. 16, next, the mutation identification unit 114 searches the mutation database 123 (step S25). Then, the mutation identification unit 114 refers to mutation information in the mutation database 123 and provides annotation to each mutation included in the result file, to identify the mutation (step S26).

FIG. 25 is a diagram showing one example of a structure of the mutation database 123 shown in FIG. 2. The mutation database 123 is constructed on the basis of the external mutation information database 3 such as COSMIC or ClinVar, for example. In one embodiment, each of mutation information in the database is provided with metadata regarding information regarding a gene panel. In the example shown in FIG. 25, each of mutation information in the database is provided with, as metadata, a gene ID of an analysis target gene.

The mutation information included in the mutation database 123 may include mutation ID, mutation position information (for example, "CHROM" and "POS"), "REF", "ALT", and "Annotation". The mutation ID is an identifier for identifying a mutation. In the mutation position information, "CHROM" indicates the chromosome number and "POS" indicates the position at the Chromosome number. "REF" indicates a base in the wild type, and "ALT" indicates a base after the mutation. "Annotation" indicates information regarding the mutation. "Annotation" may be information that indicates a mutation of an amino acid such as "EGFR C2573G", "EGFR L858R", or the like. For example, "EGFR C2573G" indicates a mutation in which cysteine at the 2573rd residue of protein "EGFR" is substituted by glycine.

As described in the example above, "Annotation" of mutation information may be information for converting a mutation according to base information into a mutation according to amino acid information. In this case, on the basis of information of "Annotation" that has been referred to, the mutation identification unit 114 can convert a mutation according to base information into a mutation according to amino acid information.

Using the information that specifies each mutation included in the result file (for example, mutation position information and base information that corresponds to the mutation) as a key, the mutation identification unit 114 searches the mutation database 123. For example, using any one of pieces of information "CHROM", "POS", "REF", and "ALT" as a key, the mutation identification unit 114 may search the mutation database 123. When a mutation extracted by comparing the alignment sequence derived from the blood specimen and the alignment sequence derived from the lesion site has been registered in the mutation database 123, the mutation identification unit 114 identifies the mutation as a mutation existing in the sample, and provides annotation (for example, "EGFR L858R", "BRAF V600E", etc.) to the mutation included in the result file.

With reference back to FIG. 16, the controller 11 outputs, through the output unit 14, information regarding which of a rearrangement sequence included in the reference sequence or the wild-type reference sequence corresponding to the rearrangement sequence matches the nucleic acid sequence determined by the sequence determination unit 113 (step S27). Specifically, the output unit 14 may output information regarding mutations identified by the mutation identification unit 114, such as the alignment result of read sequences mapped by the sequence determination unit 113 and the annotation provided to each mutation. The output unit 14 may transmit the analysis result as data. The data of the analysis result may be transmitted to the medical institution 210 or to the test institution 110 as shown in FIG. 1, for example. The output unit 14 may be a printer that is connected to the sequence analysis apparatus 1. In this case, the data of the analysis result may be printed by the printer, and then, the data in the form of a paper medium may be used by the test institution 110 or may be provided from the test institution 110 to the medical institution 210.

Alternatively, the output unit 14 may be a display that displays information regarding processes performed by the units of the controller 11. For example, read sequence information read by the read sequence information obtaining unit 111 may be displayed, and the adapter sequences and the index sequence included in the 5' end portion and the 3' end portion in each of read sequence information (see FIG. 10) may be displayed. Alternatively, the alignment result obtained by the sequence determination unit 113 may be shown as a screen display that includes the reference sequence and the read sequence information. Alternatively, information regarding mutations identified by the mutation identification unit 114 may be displayed.

As described above, a test is performed in the test institution 110, and an analysis report created on the basis of an analysis result is sent to the medical institution 210 having sent an analysis request.

The present disclosure is not limited to the embodiments described above, and various modifications can be made without departing from the scope of the claims. Embodiments obtained by combining as appropriate technological means disclosed in different embodiments are also included in the technological scope of the present disclosure.

Figure 27A:
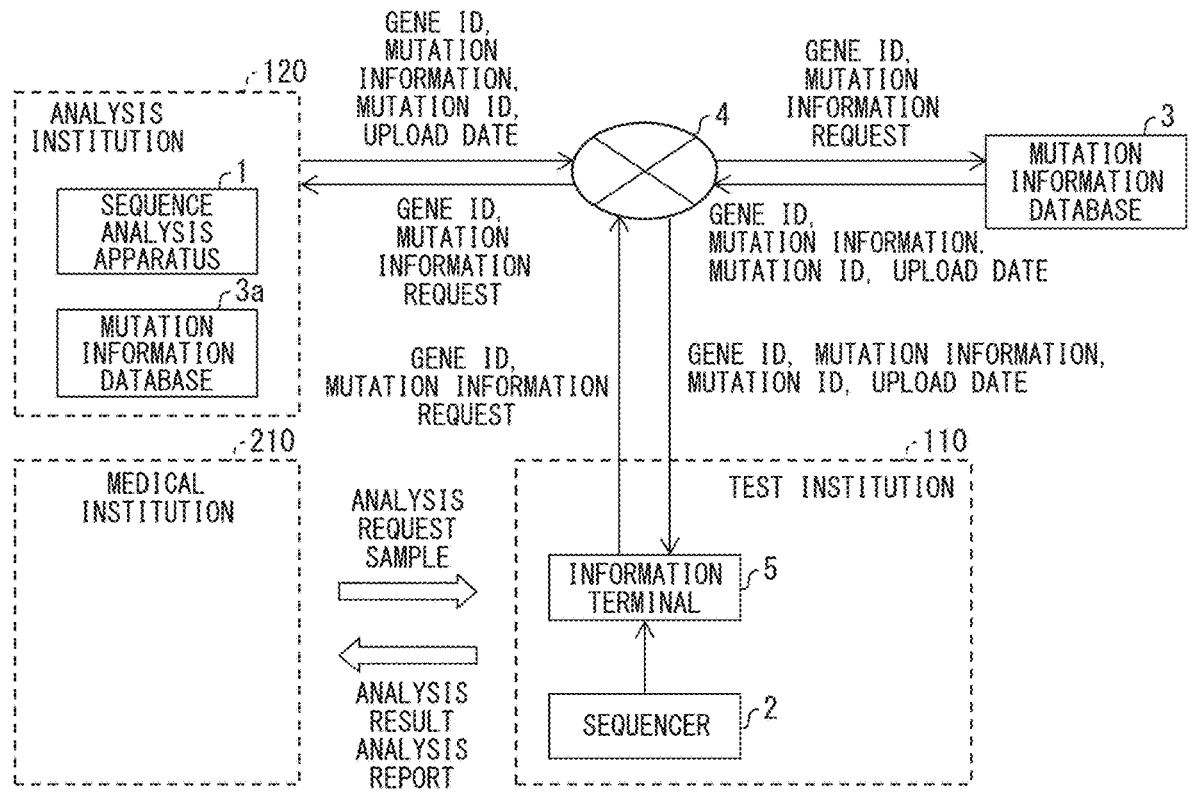
FIG. 27A is a diagram showing a modification of application of the sequence analysis apparatus.

For example, as shown in FIG. 27A, the test institution 110 may be provided with the sequencer 2, and an information terminal 5, and the like, without being provided with the sequence analysis apparatus 1, and the sequence analysis apparatus 1 may be provided in an external analysis institution 120. In this case, the information terminal 5 has: (1) a function of obtaining sequence information read by the sequencer 2; (2) a function of transmitting the information to an external institution such as, for example, the analysis institution 120 shown in FIG. 27A; (3) a function of receiving an analysis result from the analysis institution 120; and the like. The medical institution 210 may, through a network 4, transmit an analysis request to the test institution 110 and receive data of an analysis result and an analysis report.

In the test institution 110 shown in FIG. 27A, in response to an analysis request from the medical institution 210, the sequences of genes included in the sample are read by the sequencer 2. The test institution 110 transmits read sequence information having been read, to the analysis institution 120, and requests an analysis. Then, the test institution 110 receives an analysis result from the analysis institution 120, and creates an analysis report on the basis of the analysis result. The analysis report thus created is provided from the test institution 110 to the medical institution 210 which has sent the analysis request.

The mutation information database 3a shown in FIG. 27A is managed by the analysis institution 120, and may store publicly known mutation information downloaded from the external mutation information database 3, and known mutation information and the like obtained from an information source different from the external mutation information database 3.

Figure 27B:
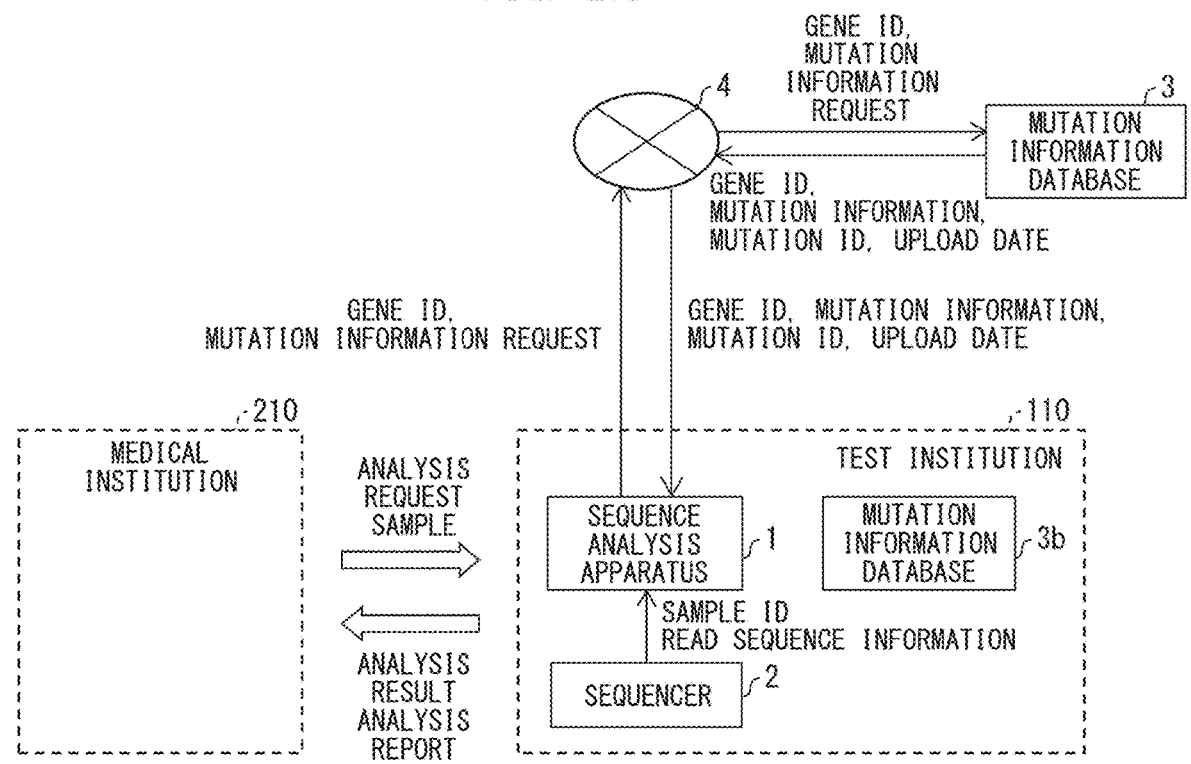
FIG. 27B is a diagram showing a modification of application of the sequence analysis apparatus.

A mutation information database 3b may be provided in the test institution 110 as shown in FIG. 27B and managed by the test institution 110. Thus, the mutation information database 3b is different from the external mutation information database 3 in that the mutation information database 3b is provided in the same institution in which the sequence analysis apparatus 1 is provided. The mutation information database 3 and the sequence analysis apparatus 1 can be connected to each other via the network 4 such as the Internet. Meanwhile, the mutation information database 3b and the sequence analysis apparatus 1 can be connected to each other via a local area network (LAN), an intranet, and the like.

The reference sequence management unit 112 shown in FIG. 2 downloads publicly known mutation information from the external mutation information database 3 to the reference sequence database 122, but the present disclosure is not limited thereto. For example, as in the analysis institution 120 shown in FIG. 27A, in an embodiment in which the mutation information database 3a which stores information regarding polymorphism, mutation, methylation, and the like downloaded from the external mutation information database 3 is provided, update of known mutation information stored in the mutation information database 3a may be performed automatically and periodically (for example, once a month, once a week, or once in two days), or may be performed as appropriate by a person who manages the mutation information database 3a. In the mutation information database 3a, known mutation information, and information indicating the date and time at which the known mutation information was stored in the mutation information database 3a may be stored in association with each other. The information indicating the date and time which is stored in association may be the date and time of update of the mutation information database.

When the sequence analysis apparatus 1 shown in FIG. 27A obtains known mutation information from the mutation information database 3a, the reference sequence management unit 112 may generate rearrangement sequences if known mutation information in the mutation information database 3a has been updated. In the mutation information database 3a, not only publicly known mutation information but also known mutation information that has not been made public may be stored. Therefore, rearrangement sequences may include not only rearrangement sequences generated on the basis of publicly known mutation information but also rearrangement sequences generated on the basis of known mutation information that has not been made public.

In the above description, an example case has been described in which the reference sequence management unit 112 generates a rearrangement sequence on the basis of known mutation information. However, the present disclosure is not limited thereto. For example, a person who belongs to the analysis institution 120 or the like may obtain known mutation information from the mutation information database 3a and generate a rearrangement sequence. The generated rearrangement sequence may be stored in the mutation information database 3a. In this case, the reference sequence management unit 112 may obtain the rearrangement sequence from the mutation information database 3a. That is, an apparatus (for example, the mutation information database 3a) that is different from the sequence analysis apparatus 1 may provide rearrangement sequences to the sequence analysis apparatus 1.

In the above description, an example case has been described in which a rearrangement sequence that corresponds to each of publicly known mutation information downloaded from the mutation information database 3 is generated by the reference sequence management unit 112 and saved in the reference sequence database 122. However, the present disclosure is not limited thereto. For example, a rearrangement sequence, a rearrangement sequence ID, a mutation ID of a mutation included in the rearrangement sequence, and the like that correspond to each of known mutation information may be stored in the mutation information database 3a, in association with one another. In this case, the reference sequence management unit 112 obtains, through the communication unit 16, a rearrangement sequence, a rearrangement sequence ID, a mutation ID of a mutation included in the rearrangement sequence, and the like that correspond to each of known mutation information, from the mutation information database 3a, and stores those in the reference sequence database 122.

The number of each of the medical institution 210, the test institution 110, and the analysis institution 120 is not limited to one. That is, the medical institution 210 may request analyses to a plurality of test institutions 110, and the test institution 110 may receive analysis requests from a plurality of medical institutions 210. The test institution 110 may request analyses to a plurality of analysis institutions 120, and the analysis institution 120 may receive analysis requests from a plurality of test institutions 110. That is, a plurality of medical institutions 210, a plurality of test institutions 110, and a plurality of analysis institutions 120 may be included. The sequence analysis apparatus 1 can be applied to an institution that has the functions of both of the medical institution 210 and the test institution 110, such as research institutes, university hospitals, and the like that have both a clinical facility and a test facility, and to an institution in which the test institution 110, the analysis institution 120, and the medical institution 210 are integrated.

For example, an apparatus that is separate from the sequence analysis apparatus 1 may have the functions of the reference sequence management unit 112 and the reference sequence generation unit 115, and the apparatus may function as a reference sequence generation apparatus that outputs rearrangement sequences and reference sequences to the sequence analysis apparatus 1. This reference sequence generation apparatus may be an external server that includes a management server 3 connected to the sequence analysis apparatus 1 via the network 4. In this case, reference sequences may be provided to the sequence analysis apparatus 1 from the external server having the function of the reference sequence generation apparatus. For example, the sequence analysis apparatus 1 may be configured as a system that includes: a first apparatus that includes the read sequence information obtaining unit 111, the sequence determination unit 113, and the mutation identification unit 114; a second apparatus that includes the reference sequence management unit 112 and the reference sequence generation unit 115; and a third apparatus (or database) that has a function similar to that of the storage unit 12.

---

What is claimed is:

1. A sequence analysis method for analyzing a nucleic acid sequence, the sequence analysis method comprising:

obtaining, by a processing device from a sequencer device, a first plurality of read sequences which are read from a first nucleic acid sequence, wherein the first plurality of read sequences comprise 40 to 200 gigabases (Gb); and at a first time, determining, by the processing device, the first nucleic acid sequence by aligning the first plurality of read sequences with reference to a single reference sequence, wherein the single reference sequence comprises at least a first rearrangement sequence and a second rearrangement sequence that is different from the first rearrangement sequence, wherein an entirety of the second rearrangement sequence is appended after an entirety of the first rearrangement sequence within the single reference sequence to form a continuous string including at least the first rearrangement sequence and the second rearrangement sequence;

the method further comprising:

at a second time after the first time, determining that a new known mutation information exists in a mutation information database, wherein a creation date for the new known mutation information corresponds to a time that is after a creation date for the single reference sequence;

updating the reference sequence to add a third rearrangement sequence related to the new known mutation information by appending an entirety of the third rearrangement sequence after at least one of the entirety of the first rearrangement sequence or the entirety of the second rearrangement sequence within the single reference sequence to create an updated single reference sequence that is formed as a continuous string including at least the first rearrangement sequence, the second rearrangement sequence, and the third rearrangement sequence;

obtaining, by the processing device from the sequencer device, a second plurality of read sequences which are read from a second nucleic acid sequence; and determining, by the processing device, the second nucleic acid sequence by aligning the second plurality of read sequences with reference to the updated single reference sequence.

2. The sequence analysis method of claim 1, wherein
the first rearrangement sequence comprises at least one of a polymorphism, a mutation, or a methylation, and
the second rearrangement sequence comprises at least one of a polymorphism, a mutation, or a methylation.

3. The sequence analysis method of claim 2, wherein
at least one of the polymorphism in the first rearrangement sequence or the polymorphism in the second rearrangement sequence is at least one of a repeat sequence polymorphism, a microsatellite, or a single nucleotide polymorphism, and
at least one of the mutation in the first rearrangement sequence or the mutation in the second rearrangement sequence is at least one of a substitution, a deletion, or an insertion.

4. The sequence analysis method of claim 1, wherein
the determining comprises comparing at least one of the plurality of the second read sequences with the updated single reference sequence, and mapping the at least one of the second plurality of read sequences to a region on the updated single reference sequence that has a highest matching rate between the at least one of the second plurality of read sequences and the updated single reference sequence.

5. The sequence analysis method of claim 1, further comprising
generating the single reference sequence that comprises the first rearrangement sequence and the second rearrangement sequence.

6. The sequence analysis method of claim 1, wherein
the first rearrangement sequence and the second rearrangement sequence are generated on the basis of known mutation information obtained from the mutation information database.

7. The sequence analysis method of claim 6, wherein
the known mutation information and information indicating when the known mutation information was obtained are associated with each other in the mutation information database.

8. The sequence analysis method of claim 1, wherein an entirety of the third rearrangement sequence is appended after the entirety of the second rearrangement sequence within the updated single reference sequence.

9. The sequence analysis method of claim 8, further comprising:
providing known mutation information stored in the mutation information database with individual identification information, and
generating the first rearrangement sequence, the second rearrangement sequence, and the third rearrangement sequence on the basis of the known mutation information respectively provided with the individual identification information.

10. The sequence analysis method of claim 1, wherein
the first rearrangement sequence is a partial sequence or a complete sequence of an exon or an intron that has at least one of a polymorphism, a mutation, or a methylation, and
the second rearrangement sequence is a partial sequence or a complete sequence of an exon or an intron that has at least one of a polymorphism, a mutation, or a methylation.

11. The sequence analysis method of claim 1, wherein
the obtaining comprises obtaining the first plurality of read sequences and the second plurality of read sequences by reading the first and second nucleic acid sequences collected with a bait.

12. The sequence analysis method of claim 1, further comprising:
reading the first plurality of read sequences and the second plurality of read sequences by using oligo DNA immobilized on a surface of a member.

13. The sequence analysis method of claim 1, wherein
the determining comprises comparing the second plurality of read sequences with a wild-type reference sequence and the updated single reference sequence.

14. The sequence analysis method of claim 1, wherein
the first rearrangement sequence is for a first gene to be analyzed and the second rearrangement sequence is for a second gene to be analyzed.

15. The sequence analysis method of claim 1, further comprising:
reading the first plurality of read sequences and the second plurality of read sequences by use of a next-generation sequencer.

16. The sequence analysis method of claim 1, further comprising:
obtaining a plurality of single reference sequences, wherein
the determining comprises aligning the plurality of read sequences with reference to each of the plurality of single reference sequences.

17. The sequence analysis method of claim 1, wherein
aligning the second plurality of read sequences with reference to the updated single reference sequence further comprises determining position information indicating a position on the updated single reference sequence at which a leftmost base of at least one of the second plurality of read sequences is mapped.

18. A sequence analysis apparatus comprising:
at least one processing device configured to:
obtain a first plurality of read sequences which are read from a first nucleic acid sequence, wherein the first plurality of read sequences comprise 40 to 200 giga-bases (Gb);
at a first time, determine the first nucleic acid sequence by aligning the first plurality of read sequences with reference to a single reference sequence, wherein the single reference sequence comprises at least a first rearrangement sequence and a second rearrangement sequence that is different from the first rearrangement sequence, wherein an entirety of the second rearrangement sequence is appended after an entirety of the first rearrangement sequence within the single reference sequence to form a continuous string including at least the first rearrangement sequence and the second rearrangement sequence;
at a second time after the first time, determine that a new known mutation information exists in a mutation information database, wherein a creation date for the new known mutation information corresponds to a time that is after the first time;
update the reference sequence to add a third rearrangement sequence related to the new known mutation information by appending an entirety of the third rearrangement sequence after at least one of the entirety of the first rearrangement sequence or the entirety of the second rearrangement sequence within the single reference sequence to create an updated single reference sequence that is formed as a continuous string including at least the first rearrangement sequence, the second rearrangement sequence, and the third rearrangement sequence;

obtain a second plurality of read sequences which are read from a second nucleic acid sequence; and determine the second nucleic acid sequence by aligning the second plurality of read sequences with reference to the updated single reference sequence.

19. The sequence analysis apparatus of claim 18, wherein the at least one processing device is configured to obtain, from the mutation information database, known mutation information to be used in generation of the first rearrangement sequence and the second rearrangement sequence.

20. A reference sequence generation apparatus configured to generate a reference sequence to be used for determining a nucleic acid sequence of a plurality of read sequences which is read by a sequencer and which comprises 40 to 200 giga-bases (Gb), the reference sequence generation apparatus comprising:

at least one processing device configured to:
obtain a first rearrangement sequence and a second rearrangement sequence;
at a first time, generate a reference sequence in which the first rearrangement sequence and the second rearrangement sequence are connected in one piece, wherein an entirety of the second rearrangement sequence is appended after an entirety of the first rearrangement sequence within the single reference sequence to form a continuous string including at least the first rearrangement sequence and the second rearrangement sequence;

at a second time after the first time, determine that a new known mutation information exists in a mutation information database, wherein a creation date for the new known mutation information corresponds to a time that is after the first time; and update the reference sequence to add a third rearrangement sequence related to the new known mutation information by appending an entirety of the third rearrangement sequence after at least one of the entirety of the first rearrangement sequence or the entirety of the second rearrangement sequence within the single reference sequence to create an updated single reference sequence that is formed as a continuous string including at least the first rearrangement sequence, the second rearrangement sequence, and the third rearrangement sequence.

21. The reference sequence generation apparatus of claim 20, wherein the at least one processing device is further configured to:

generate the updated reference sequence including a spacer sequence having a predetermined length inserted between the entirety of the first rearrangement sequence and the entirety of the second rearrangement sequence and the entirety of the third rearrangement sequence within the reference sequence.

* * * * *